(12) United States Patent
Difiore et al.

(10) Patent No.: US 11,752,242 B2
(45) Date of Patent: Sep. 12, 2023

(54) MEDICAL DEVICES, SYSTEMS, AND METHODS UTILIZING ANTITHROMBIN-HEPARIN COMPOSITION

(71) Applicants: ATH Therapeutics Inc., Alexandria, VA (US); Attilio Difiore, West Jordan, UT (US)

(72) Inventors: Attilio Difiore, West Jordan, UT (US); Leslie Roy Berry, Burlington (CA); Anthony Kam Chuen Chan, Ancaster (CA)

(73) Assignee: ATH Therapeutics Inc., Alexandria, VA (US)

( * ) Notice: Subject to any disclaimer, the term of this patent is extended or adjusted under 35 U.S.C. 154(b) by 110 days.

(21) Appl. No.: 15/735,306

(22) PCT Filed: Jun. 10, 2016

(86) PCT No.: PCT/US2016/036855
§ 371 (c)(1),
(2) Date: Dec. 11, 2017

(87) PCT Pub. No.: WO2016/201202
PCT Pub. Date: Dec. 15, 2016

(65) Prior Publication Data
US 2018/0177924 A1    Jun. 28, 2018

Related U.S. Application Data

(60) Provisional application No. 62/174,308, filed on Jun. 11, 2015.

(51) Int. Cl.
*A61L 33/00* (2006.01)
*A61L 29/16* (2006.01)
(Continued)

(52) U.S. Cl.
CPC ........ *A61L 33/0011* (2013.01); *A61K 9/0048* (2013.01); *A61K 31/727* (2013.01);
(Continued)

(58) Field of Classification Search
CPC .......... A61L 27/54; A61L 31/08; A61L 27/20; A61L 33/0011; A61F 2/00
See application file for complete search history.

(56) References Cited

U.S. PATENT DOCUMENTS

| | | | |
|---|---|---|---|
| 4,533,348 A | 8/1985 | Wolfe et al. | |
| 4,874,366 A | 10/1989 | Zdeb et al. | |

(Continued)

FOREIGN PATENT DOCUMENTS

| | | |
|---|---|---|
| CA | 1173795 A | 9/1984 |
| EP | 0353018 A1 | 1/1990 |

(Continued)

OTHER PUBLICATIONS

R1, Heparin I.V. Flush Syringe, 2012, Medefil Inc., pp. 1-6 (Year: 2012).*

(Continued)

*Primary Examiner* — Dah-Wei D. Yuan
*Assistant Examiner* — Andrew J Bowman
(74) *Attorney, Agent, or Firm* — Thorpe North & Western, LLP

(57) ABSTRACT

Medical devices, systems, and methods for treating conditions using antithrombin-heparin conjugates are disclosed. For example, medical devices can be coated with antithrombin-heparin (ATH) resulting in reduced thrombogenicity. Various conditions can likewise be treated with ATH.

19 Claims, 5 Drawing Sheets

(51) Int. Cl.

| | | |
|---|---|---|
| *A61L 31/16* | (2006.01) | |
| *A61K 47/55* | (2017.01) | |
| *A61K 47/61* | (2017.01) | |
| *A61L 27/54* | (2006.01) | |
| *A61K 47/64* | (2017.01) | |
| *A61P 27/02* | (2006.01) | |
| *A61P 7/02* | (2006.01) | |
| *A61K 9/00* | (2006.01) | |
| *A61K 31/727* | (2006.01) | |
| *A61K 38/17* | (2006.01) | |

(52) U.S. Cl.
CPC ......... *A61K 38/1709* (2013.01); *A61K 47/55* (2017.08); *A61K 47/61* (2017.08); *A61K 47/64* (2017.08); *A61L 27/54* (2013.01); *A61L 29/16* (2013.01); *A61L 31/16* (2013.01); *A61P 7/02* (2018.01); *A61P 27/02* (2018.01); *A61L 2300/42* (2013.01); *A61L 2420/02* (2013.01)

(56) References Cited

U.S. PATENT DOCUMENTS

| | | | |
|---|---|---|---|
| 4,929,242 | A | 5/1990 | Desecki et al. |
| 4,944,767 | A | 7/1990 | Barbucci et al. |
| 4,963,132 | A | 10/1990 | Gibson |
| 5,006,114 | A | 4/1991 | Rogers et al. |
| 5,024,657 | A | 6/1991 | Needham et al. |
| 5,030,203 | A | 7/1991 | Wolf, Jr. et al. |
| 5,049,139 | A | 9/1991 | Gilchrist |
| 5,098,394 | A | 3/1992 | Luther |
| 5,205,820 | A | 4/1993 | Kriesel |
| 5,395,323 | A | 3/1995 | Berglund |
| 5,547,471 | A | 8/1996 | Thompson et al. |
| 5,763,409 | A | 6/1998 | Bayol et al. |
| 5,984,373 | A | 11/1999 | Fitoussi et al. |
| 6,105,442 | A | 8/2000 | Kriesel et al. |
| 6,406,879 | B2 | 6/2002 | James et al. |
| 6,491,965 | B1 * | 12/2002 | Berry ................ A61L 27/20 427/2.1 |
| 6,702,850 | B1 | 3/2004 | Byun et al. |
| 6,805,685 | B2 | 10/2004 | Taylor |
| 7,045,585 | B2 | 5/2006 | Berry et al. |
| 7,081,109 | B2 | 7/2006 | Tighe et al. |
| 2001/0004641 | A1 | 6/2001 | Hawkins |
| 2001/0037144 | A1 * | 11/2001 | Kim ................ A61L 33/0011 623/1.15 |
| 2003/0113314 | A1 * | 6/2003 | Berry ................ A61L 27/20 424/94.64 |
| 2003/0124705 | A1 | 7/2003 | Berry et al. |
| 2005/0124970 | A1 | 6/2005 | Kunin et al. |
| 2005/0142163 | A1 * | 6/2005 | Hunter ................ A61P 1/00 424/423 |
| 2007/0003603 | A1 | 1/2007 | Karandikar et al. |
| 2007/0042015 | A1 | 2/2007 | Berry et al. |
| 2007/0212387 | A1 | 9/2007 | Patravale et al. |
| 2007/0231315 | A1 | 10/2007 | Lichte et al. |
| 2008/0027401 | A1 | 1/2008 | Ou-Yang et al. |
| 2008/0097407 | A1 | 4/2008 | Plishka |
| 2008/0131399 | A1 | 6/2008 | Ballance et al. |
| 2008/0140055 | A1 | 6/2008 | Shirley |
| 2009/0163876 | A1 | 6/2009 | Chebator et al. |
| 2009/0281059 | A1 | 11/2009 | Falotico et al. |
| 2010/0198148 | A1 | 8/2010 | Zinger et al. |
| 2010/0226963 | A1 | 9/2010 | Cooper et al. |
| 2010/0318040 | A1 | 12/2010 | Kelley, III et al. |
| 2011/0054440 | A1 | 3/2011 | Lewis |
| 2011/0066120 | A1 | 3/2011 | Lee |
| 2011/0213025 | A1 | 9/2011 | Finch, Jr. |
| 2011/0257606 | A1 | 10/2011 | Truitt et al. |
| 2012/0039843 | A1 | 2/2012 | Bos et al. |
| 2012/0083750 | A1 | 4/2012 | Sansoucy |
| 2013/0085474 | A1 | 4/2013 | Charles et al. |
| 2013/0172853 | A1 | 7/2013 | McClain et al. |
| 2013/0338644 | A1 | 12/2013 | Solomon et al. |
| 2015/0306367 | A1 | 10/2015 | DiFiore |

FOREIGN PATENT DOCUMENTS

| | | | |
|---|---|---|---|
| EP | 1663299 | A2 | 6/2006 |
| EP | 1908485 | A1 | 4/2008 |
| GB | 2187388 | A | 9/1987 |
| JP | S60-138544 | U | 9/1985 |
| JP | S62-215621 | A | 9/1987 |
| JP | 2008086604 | A | 4/2008 |
| JP | 2010516342 | A | 5/2010 |
| JP | 2013530794 | A | 8/2013 |
| WO | WO 86/03416 | A1 | 6/1986 |
| WO | WO 94/22522 | A1 | 10/1994 |
| WO | WO 9505400 | A1 | 2/1995 |
| WO | WO 2002/005873 | A2 | 1/2002 |
| WO | WO 2008/014440 | A2 | 1/2008 |
| WO | WO 2008/027000 | A2 | 3/2008 |
| WO | WO 2008/089196 | A2 | 7/2008 |
| WO | WO 2012/009456 | A1 | 1/2012 |
| WO | WO 2013/023146 | A1 | 2/2013 |
| WO | WO 2013/110956 | A1 | 8/2013 |
| WO | WO 2015/109162 | A1 | 7/2015 |

OTHER PUBLICATIONS

Klement et al., Chronic performance of polyurethane catheters covalently coated with ATH complex: A rabbit jugular vein model, 2006, Biomaterials, vol. 27, pp. 5107-5117 (Year: 2006).*

R2, Heparin Sodium Salt, 2021, ITW Reagents, pp. 1.*

E1, Heparin, 2021, Wikipedia, pp. 1-18 (Year: 2021).*

Hirsh, Low-Molecular Weight Heparin, 1998, Circulation, vol. 98, pp. 1575-1582 (Year: 1998).*

Barrowcliffe et al.; "The anticoagulant activity of heparin: measurement and relationship to chemical structure"; Journal of Pharmaceutical & Biomedical Analysis; (1989); pp. 217-226; vol. 7, No. 2.

Bauer; "Management of thrombophilia"; Journal of Thrombosis and Haemostasis; (2003); pp. 1429-1434; vol. 1; International Society on Thrombosis and Haemostasis.

Becker et al.; "Protein Chemistry and Structure: Exosites 1 and 2 are Essential for Protection of Fibrin-bound Thrombin from Heparin-catalyzed Inhibition by Antithrombin and Heparin Cofactor II"; The Journal of Biological Chemistry; (1999); pp. 6226-6233; vol. 274; <doi: 10.1074/jbc.274.10.6226.

Bedu-Addo; "Understanding Lyophilization Formulation Development"; Pharmaceutical Technology; (2004); pp. 10-18.

Berry et al.; "Inhibition of Fibrin-Bound Thrombin by a Covalent Antithrombin-Heparin Complex"; Journal of Biochemistry; (2002); pp. 167-176; vol. 132, No. 2; The Japanese Biochemical Society.

Berry et al.; "Investigation of the Anticoagulant Mechanisms of a Covalent Antithrombin-Heparin Complex"; The Journal of Biological Chemistry; (Dec. 25, 1989); pp. 34730-34736; vol. 273, No. 52; The American Society for Biochemistry and Molecular Biology, Inc.

Berry et al.; "Polypeptide-Polysaccharide Conjugates Produced by Spontaneous Non-Enzymatic Glycation"; The Journal of Biological Chemistry; (1998); pp. 434-439; vol. 124; The Japanese Biochemical Society.

Björk et al.; "Mechanism of the anticoagulant action of heparin"; Molecular and Cellular Biochemistry; (1982); pp. 161-182; vol. 48.

Chan et al.; "A novel anithrombin-heparin covalent complex: antithrombotic and bleeding studies in rabbits"; Blood Coagulation and Fibrinolysis; (1998); pp. 587-595; vol. 9, No. 7.

Chan et al.; "Antithrombin-Heparin Covalent Complex A Possible Alternative to Heparin for Arterial Thrombosis Prevention"; Circulation; (2002); pp. 261-265; vol. 106; <doi: 10.1161/01.CIR. 0000021431.88095.78 >.

Chan et al.; "Binding of heparin to plasma proteins and endothelial surfaces is inhibited by covalent linkage to antithrombin"; International Journal for Thrombosis and Haemostasis; (2004); pp. 1009-1018; vol. 91; <doi: 10.1160/TH03-06-0365 >.

(56) References Cited

OTHER PUBLICATIONS

Chan et al.; "Covalent Antithrombin-Heparin Complexes with High Anticoagulant Activity: Intravenous, Subcutaneous, and Intratracheal Administration"; The Journal of Biological Chemistry; (Aug. 29, 1997); pp. 22111-22117; vol. 272, No. 35; The American Society for Biochemistry and Molecular Biology, Inc.

Chan et al.; "Decreased Concentrations of Heparinoids are Required to Inhibit Thrombin Generation in Plasma from Newborns and Children Compared to Plasma from Adults due to Reduced Thrombin Potential"; Journal of Thrombosis and Haemostasis; (2002); pp. 606-613; vol. 87.

Chan et al.; "Isoform composition of antithrombin in a covalent antithrombin-heparin complex"; Biochemical and Biophysical Research Communications; (2003); pp. 986-991; vol. 309; <doi: 10.1016/j.bbrc.2003.08.109 >.

Chander et al.; "Interactions of heparin and a covalently-linked antithrombin-heparin complex with components of the fibrinolytic system"; Blood Coagulation, Fibrinolysis and Cellular Haemostasis; (2013); pp. 1180-1188; vol. 110; <doi: 10.1160/TH13-04-0290 >.

Chang et al.; "Inhibition of Plasmin Generation in Plasma by Heparin, Low Molecular Weight Heparin and a Covalent Antithrombin-Heparin Complex (ATH)"; Blood; (2014); 4217 pages; vol. 124, Issue 21; American Society of Hematology.

Chindemi et al.; "Biodistribution of covalent antithrombin-heparin complexes"; Blood Coagulation, Fibrinolysis and Cellular Haemostasis; (2006); pp. 629-636; vol. 95.

Du et al.; "Chemical-Physical Characterization of Polyurethane Catheters Modified with a Novel Antithrombin-Heparin Covalent Complex"; Journal of Biomaterials Science; (2011); pp. 2277-2294; vol. 22; <doi: 10.1163/092050610X538227 >.

Du et al.; "Protein adsorption on polyurethane catheters modified with a novel antithrombin-heparin covalent complex"; Journal of Biomedical Materials Research Part A; (2006); pp. 216-225; <doi: 10.1002/jbm.a>.

Holmer et al.; "The molecular-weight dependence of the rate-enhancing effect of heparin on the inhibition of thrombin, Factor Xa, Factor IXa, Factor XIa, Factor XIIa and kallikrein by antithrombin"; Journal of Biochemistry; (1981); pp. 395-400; vol. 193.

Johnson et al.; "Mannitol-Sucrose Mixtures—Versatile Formulations for Protein Lyophilization"; Journal of Pharmaceutical Sciences; (Apr. 2002); pp. 914-922; vol. 91, No. 4.

Klement et al.; "Blood-compatible biomaterials by surface coating with a novel antithrombin-heparin covalent complex"; Biomaterials; (2002); pp. 527-535; vol. 23; Elsevier.

Klement et al.; "Chronic performance of polyurethane catheters covalently coated with ATH complex: A rabbit jugular vein model"; Biomaterials; (2006); pp. 5107-5117; vol. 27; Elsevier.

Leung et al.; "Surface modification of polydimethylsiloxane with a covalent antithrombin-heparin complex to prevent thrombosis"; Journal of Biomaterials Science, Polymer Edition; (2014); pp. 786-801; vol. 25, No. 8.

MacLean et al.; "Hereditary and Acquired Antithrombin Deficiency Epidemiology, Pathogenesis and Treatment Options"; Drugs; (2007); pp. 1429-1440; vol. 67, No. 10.

Mann et al.; "Citrate anticoagulation and the dynamics of thrombin generation"; Journal of Thrombosis and Haemostasis; (2007); pp. 2055-2061; vol. 5; International Society on Thrombosis and Haemostasis.

Mewhort-Buist et al.; "Structural Effects of a Covalent Linkage Between Antithrombin and Heparin: Covalent N-Terminus Attachment of Heparin Enhances the Maintenance of Antithrombin's Activated State"; Journal of Biochemistry; (2006); pp. 175-184; vol. 140; <doi: 10.1093/jb/mvj139 >.

Opatrný et al.; "Citrate Anticoagulation Control by Ionized Calcium Levels Does Not Prevent Hemostasis and Complement Activation During Hemodialysis"; Artifical Organs; (2007); pp. 200-207; vol. 31, No. 3.

Parades et al.; "Mechanisms Responsible for Catalysis of the Inhibition of Factor Xa or Thrombin by Antithrombin Using a Covalent Antithrombin-Heparin Complex"; The Journal of Biological Chemistry; (Jun. 27, 2003); pp. 23398-23409; vol. 278, No. 26; <doi: 10.1074/jbc.M302895200 >.

Parmar et al.; "Effect of covalent antithrombin-heparin complex on developmental mechanisms in the lung"; American Journal of Physiology-Lung Cellular and Molecular Physiology; (2009); pp. L394-L403; vol. 296; <doi: 10.1152/ajplung.00066.2008 >.

Patel et al.; "Analysis of Inhibition Rate Enhancement by Covalent Linkage of Antithrombin to Heparin as a Potential Predictor of Reaction Mechanism"; Journal of Biochemistry; (2007); pp. 25-35; vol. 141; <doi: 10.1093/jb/mvm001 >.

Project BT-89; "Non-covalent ATH coating and Washings of the Solomon tFr catheters with ATH (1mg/mL)/125IATH"; Notebook No. 4; (2002); 10 pages.

Rezaie et al.; "Calcium Enhances Heparin Catalysis of the Antithrombin—Factor Xa Reaction by Promoting the Assembly of an Intermediate Heparin—Antithrombin—Factor Xa Bridging Complex. Demonstration by Rapid Kinetics Studies"; Biochemistry; (2000); pp. 12083-12090; vol. 39; American Chemical Society.

Sask et al.; "Modification of Polyurethane Surface with an Antithrombin-Heparin Complex for Blood Contact: Influence of Molecular Weight of Polyethylene Oxide Used as a Linker/Spacer"; Langmuir; (2012); pp. 2099-2106; vol. 28; American Chemical Society; <doi: dx.doi.org/10.1021/la203821g >.

Sask et al.; "Polyurethane modified with an antithrombin-heparin complex via polyethylene oxide linker/spacers: Influence of PEO molecular weight and PEO-ATH bond on catalytic and direct anticoagulant functions"; Journal of Biomedical Materials Research Part A; (2012); pp. 2821-2828; vol. 100A;<doi: 10.1002/jbm.a.34218 >.

Sask et al.; "Surface modification with an antithrombin-heparin complex for anticoagulation: Studies on a model surface with gold as substrate"; Acta Biomaterialia; (2010); pp. 2911-2919; vol. 6; Elsevier; <doi: 10.1016/j.actbio.2010.02.043 >.

Smith et al.; "An Antithrombin-Heparin Complex Increases the Anticoagulant Activity of Fibrin Clots"; Research Letters in Biochemistry; (2008); 4 pages; vol. 2008, Article ID 639829; <doi: 10.1155/2008/639829 >.

Spiess; "Treating Heparin Resistance With Antithrombin or Fresh Frozen Plasma"; The Annals of Thoracic Surgery; (2008); pp. 2153-2160; vol. 85; The Society of Thoracic Surgeons; <doi: 10.1016/j.athoracsur.2008.02.037 >.

Stevic et al.; "Covalently linking heparin to antithrombin enhances prothrombinase inhibition on activated platelets"; Blood Coagulation, Fibrinolysis and Cellular Haemostasis; (2013); pp. 1016-1024; vol. 109; <doi: 10.1160/TH12-10-0766 >.

Stevic et al.; "Mechanism of inhibition of the prothrombinase complex by a covalent antithrombin-heparin complex"; Journal of Biochemistry; (2012); pp. 139-148; vol. 152, No. 2; <doi: 10.1093/jb/mvs039 >.

Van Walderveen et al.; "Effect of covalent antithrombin-heparin on activated protein C inactivation by protein C inhibitor"; Journal of Biochemistry; (2010); pp. 255-260; vol. 148, No. 2; <doi: 10.1093/jb/mvq060 >.

Yoshimura et al.; "On the Catalysis of the Amadori Rearrangement"; Carbohydrate Research; (1969); pp. 276-281; vol. 11, Issue 2; Elsevier Publishing Company, Amsterdam, Belgium.

Petitou et al.; "Antithrombotics: A Synthetic Antithrombin III Binding Pentasaccharide Is Now a Drug! What Comes Next?"; Angewandte Chemie International Edition; (2004); pp. 3118-3133; vol. 43, Issue 24; <doi: 10.1002/anie.200300640 >.

De Cock et al.; "Topical Heparin in the Treatment of Ligneous Conjunctivitis"; Ophthalmology; (Oct. 31, 1995); pp. 1654-1659; vol. 102, No. 11; <doi: pubmed: 9098258 >.

Fine et al.; "Successful Treatment of Ligneous Gingivitis with Warfarin"; Oral Surgery, Oral Medicine, Oral Pathology, Oral Radiology; (Jan. 1, 2009); pp. 77-80; vol. 107, No. 1; <doi: 10.1016/j.tripleo.2008.08.007 >.

Pletcher et al., Molecular Weight Analysis of Antithrombin III-Heparin and Antithrombin III-Thrombin-Heparin Complexes, The Journal of Biological Chemistry, vol. 261, No. 9, pp. 4143-4147, Mar. 25, 1986.

* cited by examiner

MEDICAL DEVICES, SYSTEMS, AND METHODS UTILIZING ANTITHROMBIN-HEPARIN COMPOSITION

BACKGROUND

Coagulation, or clotting, is the process by which blood changes from a liquid to a gel state. This is a part of hemostasis, or the process by which the body stops blood loss from damaged blood vessels. Although clotting is a known function of the human body, clotting can result in difficult problems during medical procedures such as surgery and intravenous or intra-arterial catheterization. A sizable portion of the population also may experience clotting disorders in which unwanted blood clots create dangerous health risks.

Invasive procedures, such as cardiopulmonary bypass (CPB), induce massive amounts of fibrin microemboli that can lodge in the brain, potentially leading to long-term cognitive dysfunction. CPB is performed worldwide to treat cardiovascular disease. The use of CPB in the pediatric arena is a specialized and sensitive operation. Approximately 750 pediatric surgeries are performed in Canada each year, and 7,500 in the USA or Europe. Including adult surgeries there are over 800,000 performed world-wide each year. The estimated cost for a single CPB surgery in Canada is over $10,000. Currently heparin is the drug of choice in CPB and the cost per year is approximately $50/CPB, or $40,000,000 annually. Heparin is unable to prevent thromboemboli from traveling to the brain during CPB, which is associated with acute and chronic cognitive dysfunction. Thromboemboli are also a risk factor in many other invasive surgeries. Uncontrolled bleeding after CPB is a major concern for care of such high risk patients.

Venous thromboembolism (VTE) is another condition associated with unwanted blood clotting. VTE affects 1-2 per 1000 people each year, usually in the form of deep venous thrombosis (DVT) of the leg, or pulmonary embolism (PE). The incidence rate increases from 1 in 10,000 for individuals younger than 40 years, to 1 in 100 for those older than 60 years. Approximately 1 million individuals develop DVT each year in the U.S., and an additional 500,000 develop PE, of which 30% are fatal. Overall, approximately two-thirds of all VTE cases require hospitalization. In a study of 66,000 patients with adult neutropenic cancer, there was a substantially higher inpatient mortality rate amongst cancer patients who developed VTE (14.85%) compared to those who did not (7.98%). VTE was also named responsible for 46.3% of all deaths following cancer surgery. In the UK, the government estimated that more than 25,000 deaths occur each year due to VTE, greater than the number of deaths from breast cancer, HIV, and road traffic accidents combined. It is anticipated that cases of VTE will rise due to the aging of the general population, and increased exposure to risk factors such as surgery, oral contraceptives, long distance travelling, and higher levels of obesity.

Plasminogen deficiency is a well-recognized disorder where reduced levels of plasminogen lead to the development of pseudo membranes on mucosal surfaces. One such condition is ligneous conjunctivitis. Ligneous conjunctivitis is another example of a disease involving harmful clotting. Pediatric patients with a mutation leading to homozygous plasminogen deficiency have phenotypic expression of a membrane over their eyes (ligneous conjunctivitis) formed from coagulation leading to fibrin clot formation. These pseudomembranous lesions of the eyes can cause chronic ocular problems that can be severe to the extent of essentially complete visual impairment. As of 2003, over 100 children with this affliction had been reported worldwide but many more have been identified in recent years. The current treatment is frequent scraping of the cornea. However, these surgical manipulations do not give lasting relief and remodeling of the surface epithelial layers can give permanent damage affecting eye function. Long-term progression of the disease, even with intermittent physical removal, can lead to reduced physical development and hindrance of the learning process in the affected child. Thus, apart from the significant physical suffering borne by the individual, this is a very serious problem strongly impacting the child's health through their entire lifetime. It would be highly desirable if a non-invasive method could be devised that would save the eyesight of these patients. Current values for the number of patients affected by ligneous conjunctivitis are not known. However, a study in 1996 found the prevalence of heterozygous type I plasminogen deficiency to be 0.25% (25 of 9611 subjects), which corresponds with a homozygous/compound-heterozygous prevalence of 1.6 per 1 000 000 people. Topical treatments with corticosteroids, hyaluronidase, and antibiotics have shown variable success. Surgical intervention to excise the ligneous mass is commonly performed, but does little to prevent the recurrence of the condition necessitating repeat procedures.

Respiratory distress syndrome (RDS) is a common disorder involving fibrosis in the lungs. Approximately 1% of all infants are born at a weight less than 1500 grams and the majority of these suffer from RDS. Infants with birth weights less than 1000 grams have very large incidences of RDS and 50-80% of these infants either die or develop bronchopulmonary dysplasia (BPD). In fact, RDS is still the leading cause of mortality and morbidity in preterm newborns. Although use of surfactant has decreased the severity and slightly improved the mortality of RDS in premature infants, there is still significant RDS/BPD incidence and BPD severity. In the case of both children and adults, infection, environmental factors and genetic components can provoke acute RDS episodes that progress to chronic dysfunctional disease states involving remodeling of lung tissue and structures.

Lung damage is an event that has major impact on quality of life and can give significant mortality risk. Underlying causes of lung injury that have been shown follow from both acute and chronic factors. Recently, there has been growing recognition that mechanical damage due to high lung stress is a significant contributor to pulmonary injury occurrence. Assisted breathing treatment given through mechanical ventilation may give trauma that can incite progression of localized injury in acute RDS patients. Although low tidal volume may give improved outcomes, mortality remains unacceptably high. Indeed, in its own right, ventilators can directly give lung damage and reports are now highlighting biological markers of ventilation-associated lung injury. Behind the basic pathways leading to clinical lung damage, there is an increasing awareness of associations with new interlocking mechanisms. Very recently, strong evidence is emerging that coagulation, triggered by initial lung injury, contributes to development of pulmonary inflammation and fibrosis in acute RDS. Upregulation of coagulant tissue factor (TF) is a marker associated with RDS development. For some time it has been known that alveolar fibrin deposition may predispose infants to BPD complications, although fibrin-related damage during RDS/BPD is not always obvious due to its rapid clearance from the lung. Nevertheless, even in the absence of cross-linked fibrin clot, low levels of fibrin monomer products interfere with surfactant function and assist in alveolar surface remodeling and fibrosis due to recruitment of fibroblasts. In a similar way, relationships between ventilation-induced lung injury and coagulation are also being recognized. Again, increased TF expression resultant from ventilatory insult is suggested as a factor in thrombotic complications leading to progression in lung damage. High tidal volume ventilation treatment can, itself, induce TF-associated pulmonary and systemic coagulation in newborns.

Blood clotting can also cause problems with blood-contacting devices such as catheters and stents. These devices tend to suffer device failure due to surface-induced thrombosis. Clotting is a significant clinical problem with central venous access catheters. Catheters are used to draw blood and deliver medications to numerous patients with a variety of conditions who need regular and long-term venous access. Ideally, it should be possible to leave a catheter in place for months or even years, but catheters are notorious for clotting. In fact, in the case of children the vast majority of thrombosis is catheter-related. For example, 89% of venous and arterial thromboses in neonates involve an intravascular catheter, and 78% of aortic thromboses in children are catheter associated. One study concluded that presence of a catheter was the highest risk factor for thrombosis in children. In total, for patients of all ages that receive venous catheters, up to 26% have catheter-related thrombotic complications. Although the mechanism of surface-induced thrombosis has not been fully elucidated, it is believed that protein adsorption takes place soon after the surface contacts blood, followed by platelet adhesion and activation, as well as leukocyte activation, which ultimately results in formation of a clot. Thrombi formed inside a catheter lumen, render the catheter unusable for withdrawing blood or delivering fluids and medication. Clots forming on the outside of the catheter can lead to deep vein thrombosis and embolization, and can damage the integrity of the vessel, leading to pain and swelling. Both of these situations cause discomfort for the patient, disrupt patient care and increase the resources needed for care. Treatment for an occluded catheter involves either thrombolytic therapy, or replacement of the catheter. This results in increased inconvenience and discomfort to the patient, as well as increased cost for their treatment.

Central venous catheter (CVC) replacement is a very invasive procedure which causes patients to experience pain and prolonged hospital stays, and prevents physicians from having sufficient time to serve other patients because of replacement surgeries. Patient care also suffers because patients should have treatment interrupted or stopped due to failure of their CVC. Clots on CVCs can also break off and travel through the blood stream to other parts of the body, causing severe complications. Therefore, these clots may lead to prolonged hospital stay, interruption in essential patient treatment, neuro-cognitive dysfunction and even death.

The ageing of the population is expected to result in an increased incidence of coronary artery disease, heart failure and stroke. Therefore, the problems caused by clotting-related diseases, unwanted clotting on medical devices, and clotting during medical procedures are expected to increase, which will produce a huge financial burden in the health care industry.

Figure 1A:
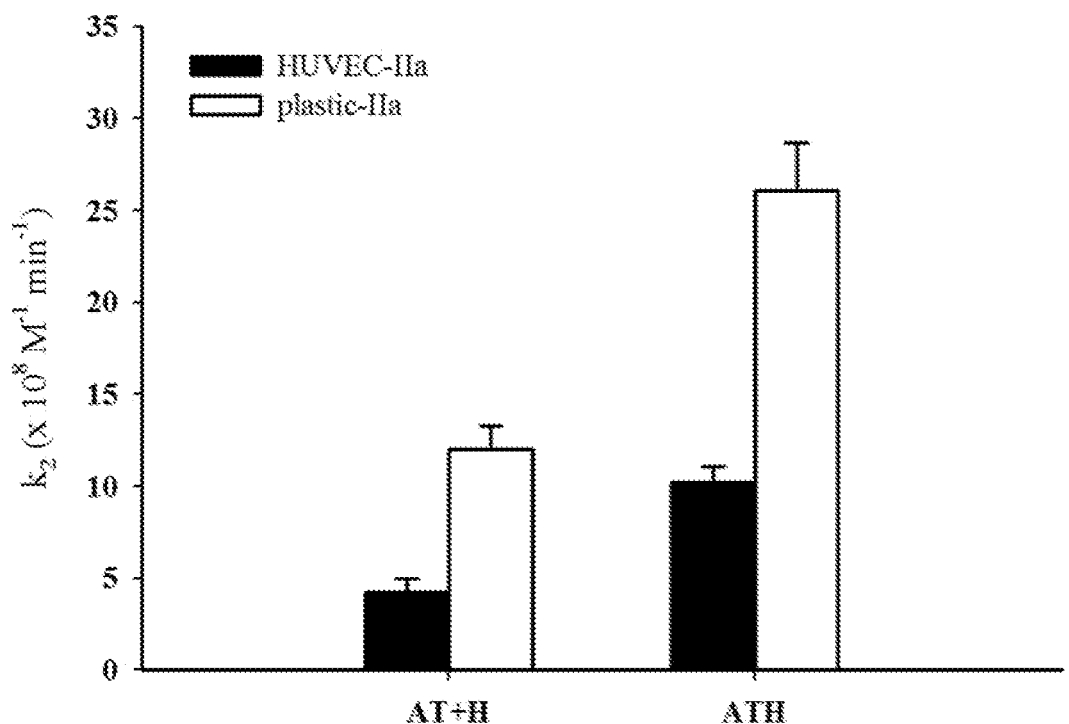
FIG. 1A is a graph of second order rate constant ($k_2$) values for ATH and non-covalent AT+H inhibition of IIa in accordance with examples of the present disclosure.

It should be noted that the figures are merely exemplary of several embodiments and no limitations on the scope of the present technology are intended thereby.

DETAILED DESCRIPTION

Reference will now be made to exemplary embodiments and specific language will be used herein to describe the same. It will nevertheless be understood that no limitation of the scope of the disclosure is thereby intended. Alterations and further modifications of the inventive features described herein, and additional applications of the principles of the technology as described herein, which would occur to one skilled in the relevant art and having possession of this disclosure, are to be considered within the scope of the disclosure. Further, before particular embodiments are disclosed and described, it is to be understood that this disclosure is not limited to the particular process and materials disclosed herein as such may vary to some degree. It is also to be understood that the terminology used herein is used for the purpose of describing particular embodiments only and is not intended to be limiting, as the scope of the present disclosure will be defined only by the appended claims and equivalents thereof.

In describing and claiming the present technology, the following terminology will be used.

The singular forms "a," "an," and "the" include plural references unless the context clearly dictates otherwise. Thus, for example, reference to "an additive" includes reference to one or more of such components, "a solution" includes reference to one or more of such materials, and "a mixing step" refers to one or more of such steps.

As used herein, "substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context.

As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" expressly includes "exactly," consistent with the discussion below regarding ranges and numerical data.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and 200, but also to include individual sizes such as 2, 3, 4, and sub-ranges such as 10 to 50, 20 to 100, etc.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, "hexose" refers to a carbohydrate ($C_6H_{12}O_6$) with six carbon atoms. Hexoses may be aldohexoses such as, for example, glucose, mannose, galactose, idose, gulose, talose, allose and altrose, whose open chain form contains an aldehyde group. Alternatively, hexoses may be ketoses such as fructose, sorbose, allulose and tagatose, whose open chain form contains a ketone group.

As used herein, "uronic acid" refers to the carboxylic acid formed by oxidation of the primary hydroxyl group of a carbohydrate and are typically named after the carbohydrate from which they are derived. Therefore, oxidation of the C6 hydroxyl of glucose gives glucuronic acid, oxidation of the C6 hydroxyl of galactose gives galacturonic acid and oxidation of the C6 hydroxyl of idose gives iduronic acid.

As used herein, "hexosamine" refers to a hexose derivative in which at least one hydroxy group, typically the C2 hydroxy group, has been replaced by an amine. The amine may be optionally alkylated, acylated (such as with muramic acid), typically by an acetyl group, sulfonated (N-sulfated), sulfonylated, phosphorylated, phosphonylated and the like. Representative examples of hexosamines include glucosamine, galactosamine, tagatosamine, fructosamine, their modified analogs and the like.

As used herein, "glycosaminoglycan" refers to linear chains of largely repeating disaccharide units containing a hexosamine and a uronic acid. The precise identity of the hexosamine and uronic acid may vary widely and representative examples of each are provided in the definitions above. The disaccharide may be optionally modified by alkylation, acylation, sulfonation (O- or N-sulfated), sulfonylation, phosphorylation, phosphonylation and the like. The degree of such modification can vary and may be on a hydroxy group or an amino group. Most usually, the C6 hydroxyl and the C2 amine are sulfated. The length of the chain may vary and the glycosaminoglycan may have a molecular weight of greater than 200,000 Daltons, typically up to 100,000 Daltons, and more typically less than 50,000 Daltons. Glycosaminoglycans are typically found as mucopolysaccharides. Representative examples include, heparin, dermatan sulfate, heparan sulfate, chondroitin-6-sulfate, chondroitin-4-sulfate, keratan sulfate, chondroitin, hyaluronic acid, polymers containing N-acetyl monosaccharides (such as N-acetyl neuraminic acid, N-acetyl glucosamine, N-acetyl galactosamine, and N-acetyl muramic acid) and the like and gums such as gum arabic, gum Tragacanth and the like.

"Heparin" is a sulfated polysaccharide which consists largely of an alternating sequence of hexuronic acid and 2-amino-2-deoxy-D-glucose. Heparin and a related compound, dermatan sulfate, work well as anticoagulants for clinical use in the prevention of thrombosis and related diseases. They are members of the family of glycosaminoglycans, (GAGs), which are linear chains of sulfated repeating disaccharide units containing a hexosamine and a uronic acid. Anticoagulation using GAGs (such as heparin and dermatan sulfate) proceeds via their catalysis of inhibition of coagulant enzymes (a significant one being thrombin) by serine protease inhibitors (serpins) such as antithrombin III (referred to herein as simply "antithrombin" or "AT") and heparin cofactor II (HCII). Binding of the serpins by the catalysts occurs for their action and occurs through specific sequences along the linear carbohydrate chain of the glycosaminoglycan (GAG). Heparin acts by binding to AT via a pentasaccharide sequence, thus potentiating inhibition of a variety of coagulant enzymes (in the case of thrombin, heparin also binds to the enzyme). Heparin can also potentiate inhibition of thrombin by binding to the serpin HCII. Dermatan sulfate acts by specifically binding to HCII via a hexasaccharide sequence, thus potentiating only the inhibition of thrombin. Since glycosaminoglycans (particularly heparin) can bind to other molecules in vivo or be lost from the site of action due to a variety of mechanisms, it would be advantageous to keep the GAG permanently associated with the serpin by a covalent bond. In further detail, it would be desirable to provide covalent conjugates of heparin and related glycosaminoglycans which retain high biological activity (e.g., anticoagulant activity) and improved pharmacokinetic properties and simple methods for their preparation.

As used herein, "protein" includes, but is not limited to, albumins, globulins (e.g., immunoglobulins), histones, lectins, protamines, prolamines, glutelins, phospholipases, antibiotic proteins and scleroproteins, as well as conjugated proteins such as phosphoproteins, chromoproteins, lipoproteins, glycoproteins, nucleoproteins.

As used herein, "serpin" refers to a serine protease inhibitor and is exemplified by species such as antithrombin and heparin cofactor II.

As used herein, "amine" refers to primary amines, $RNH_2$, secondary amines, $RNH(R')$, and tertiary amines, $RN(R')(R'')$.

As used herein, "amino" refers to the group NH or $NH_2$.

As used herein, "imine" refers to the group C=N and salts thereof.

As used herein, the terms "treatment" or "treating" of a condition and/or a disease in a mammal, means: preventing the condition or disease, that is, avoiding any clinical symptoms of the disease; inhibiting the condition or disease, that is, arresting the development or progression of clinical symptoms; and/or relieving the condition or disease, that is, causing the regression of clinical symptoms. Treatment also includes use of the compositions of the present disclosure associated with a medical procedure with administration before, during or after the medical procedure.

In accordance with the background described above, the present disclosure is drawn to methods and compositions for treating conditions involving clotting. In one example, a method of coating a polymeric surface with an antithrombin-heparin conjugate can include contacting the polymeric surface with a solution of antithrombin-heparin conjugate. The antithrombin-heparin conjugate can directly coat the polyurethane surface without linking groups between the antithrombin-heparin conjugate and the polymeric surface.

In another example, a medical device having reduced thrombogenicity can include a polymeric surface coated with an antithrombin-heparin conjugate without linking groups between the antithrombin-heparin conjugate and the polymeric surface.

In a further example, a method of lyophilization coating a polymeric surface of a medical device can include contacting the polymeric surface of the medical device with an antithrombin-heparin solution comprising antithrombin-heparin conjugate and a solvent in the absence of linking groups. Then, excess antithrombin-heparin solution can be allowed to drain off the polymeric surface. Solvent can then be evaporated from the polymeric surface under at least partial vacuum.

An additional example involves a method of treating a medical condition by inhibiting thrombogenesis in a mammal. The method can include administering a dose of an antithrombin-heparin conjugate to the mammal, wherein at least 98% of heparin chains in the antithrombin-heparin conjugate have a molecular weight greater than 3,000 Daltons.

In another example, a method of treating ligneous conjunctivitis in a mammal can include administering a dose of an antithrombin-heparin conjugate to an eye of the mammal.

In yet another example, a method of treating an injury from mechanical ventilation in a mammal can include administering a dose of an antithrombin-heparin conjugate to an injured lung of the mammal.

In an additional example, a method of treating ligneous gingivitis in a mammal can include administering a dose of an antithrombin-heparin conjugate to gums of the mammal.

In a separate example, a solution for flushing and locking an intravenous or intra-arterial catheter can include an antithrombin-heparin conjugate.

Another example involves a method of maintaining patency of a catheter. The method can include inserting a catheter into a vein or artery of a subject so that an interior opening of the catheter opens inside the vein or artery and an exterior opening of the catheter opens outside the subject. A solution comprising an antithrombin-heparin conjugate can be injected into the catheter through the exterior opening of the catheter. Then, the exterior opening of the catheter can be sealed such that at least a portion of the solution comprising the antithrombin-heparin conjugate remains within the catheter.

In yet another example, a composition for treating blood clots can include antithrombin, heparin, and fibrin. At least 50 wt % of the heparin can be conjugated to antithrombin to form an antithrombin-heparin conjugate. At least a portion of the fibrin can be bound to antithrombin-heparin conjugate.

In another example, a method of treating a condition or disease can include administering an antithrombin-heparin conjugate prepared in accordance with examples of the present technology to a mammal in need thereof. In further detail, these treatments can be carried about by administering the heparin and antithrombin conjugates of the present disclosure to a subject, such as a human, in need of such a treatment. Conditions and diseases that can be treated using the conjugate compositions described herein include myocardial infarction and a large array of thrombotic states. These include fibrin deposition found in neonatal respiratory distress syndrome, adult respiratory distress syndrome, primary carcinoma of the lung, non-Hodgkins lymphoma, fibrosing alveolitis, and lung transplants, to name a few. Also, the present compositions can treat either acquired AT deficient states such as neonatal respiratory distress syndrome, L-asparaginase induced deficiency, cardiopulmonary bypass induced deficiency, sepsis or congenital AT deficient states. In the case of congenital AT deficiency, life threatening thrombotic complications with AT levels of less than 0.25 Units/ml in heterozygotes requiring AT plus heparin may occur in up to 1 or 2 infants per year in the U.S.A. The conditions and diseases treated in the present disclosure include those characterized by excess thrombin generation or activity. Such conditions often occur where a subject has been exposed to trauma, for example in surgical patients. Trauma caused by wounds or surgery results in vascular damage and secondary activation of blood coagulation. These undesirable effects may occur after general or orthopedic surgery, gynecologic surgery, heart or vascular surgery, or other surgical procedures. Excess thrombin may also complicate progression of natural diseases such as atherosclerosis which can cause heart attacks, strokes or gangrene of the limbs. Therefore, the methods and compositions of the present technology can be used to treat, prevent, or inhibit a number of cardiovascular complications, including unstable angina, acute myocardial infarction (heart attack), cerebral vascular incidents (stroke), pulmonary embolism, deep vein thrombosis, arterial thrombosis, etc. The compositions and methods of the technology may be used to reduce or prevent clotting during dialysis and reduce or prevent intravascular coagulation during open heart surgical procedures. In additional detail, in aspects of the disclosure, methods and compositions are provided for preventing or inhibiting thrombin generation or activity in patients at increased risk of developing a thrombus due to medical conditions that disrupt hemostasis (e.g., coronary artery disease, atherosclerosis, etc.). In another aspect, methods and compositions are provided for patients at increased risk of developing a thrombus after a medical procedure, such as cardiac surgery, vascular surgery, or percutaneous coronary interventions. In an embodiment, the methods and compositions of this disclosure are used in cardiopulmonary bypass surgery. The compositions can be administered before, during or after the medical procedure.

Turning now to the antithrombin-heparin conjugate used in the compositions and treatments described in the present disclosure, the antithrombin-heparin conjugate provides several advantages over heparin as an antithrombotic.

Antithrombin-heparin conjugate (ATH) can be prepared by covalent attachment of heparin chains to antithrombin (AT). Heparin contains aldose termini which coexist in an equilibrium between hemiacetal and aldehyde forms. Heparin can be conjugated to antithrombin by reduction of the single Schiff base formed spontaneously between the aldose terminus aldehyde on heparin and a lysyl or N-terminal amino on the antithrombin. The heparin is unmodified (unreduced in activities) prior to conjugation and is linked at one specific site at one end of the molecule without any unblocked activation groups or crosslinking of the antithrombin.

The reaction is typically carried out at a pH of about 4.5 to about 9, or at about 5 to about 8, or even at about 7 to about 8. The reaction is generally done in aqueous media. However, organic media, especially polar hydrophilic organic solvents such as alcohols, ethers and formamides and the like may be employed in proportions of up to about 40% to increase solubility or reactivity of the reactants, if necessary. Non-nucleophilic buffers such as phosphate, acetate, bicarbonate and the like may also be employed.

Imines formed by condensation of the amines of the AT with the terminal aldose residues of the heparin can be reduced to the corresponding amines. This reduction may be accomplished concurrently with imine formation or subsequently. A wide array of reducing agents may be used, with hydride reducing agents, such as for example, sodium borohydride or sodium cyanoborohydride being specific examples that are useful. Generally, any reducing agent that does not reduce disulfide bonds can be used.

Alternatively, if reduction of the intermediate imine is not desired, the imine may be incubated for a sufficient period of time, typically about 1 day to 1 month, more typically about 3 days to 2 weeks, to allow Amadori rearrangement of the intermediate imine. The terminal aldose residues of the heparin conjugated by the methods provided by this invention can possess C2 hydroxy groups on the terminal aldose residue, i.e., a 2-hydroxy carbonyl moiety which is converted to a 2-hydroxy imine by condensation with the amine of the AT being conjugated to the heparin. In the Amadori rearrangement, the α-hydroxy imine (imine at C1, hydroxy at C2) formed by the initial condensation may rearrange to form an α-keto amine by enolization and re-protonation (keto at C2, amine at C1). The resulting α-carbonyl amine is thermodynamically favored over the precursor α-hydroxy imine, thus providing a stable adduct with minimal disruption of the heparin chain. Thus, heparin can be covalently conjugated at the C1 of the terminal aldose residue of the heparin to an amine-containing AT chain via an amine linkage. Covalent complexes can be formed by simply mixing heparin and AT in buffer and allowing a keto-amine to spontaneously form by an Amadori rearrangement between the heparin aldose terminus and an AT lysyl or N-terminal amino group. Thus, the Amadori rearrangement can be used to prepare conjugates of heparin to AT. This is a particularly mild and simple method of conjugation, which minimizes the modification of the glycosaminoglycan, thus maximizing the retention of its biological activity.

Antithrombin-heparin conjugate can, in some cases, be prepared using unfractionated heparin. In other cases, antithrombin-heparin conjugate can be prepared using heparin from which low molecular weight heparin chains have been removed. It is known that heparin is readily available in an unfractionated form, which contains molecules with a wide range of molecular weights. By removing from most to all of the heparin molecules having molecular weights less than 3,000 Daltons prior to conjugating the heparin with the antithrombin, the activity of the antithrombin-heparin conjugate can be enhanced. In an additional embodiment, heparin molecules having a molecular weight less than 5,000 Daltons can be from mostly to completely removed prior to conjugation with antithrombin.

The antithrombin-heparin conjugates formed using heparin from which low molecular weight heparin molecules have been removed are compositionally different from other antithrombin-heparin conjugates. Low molecular weight heparin chains can be removed from the heparin prior to reaction with AT to synthesize the antithrombin-heparin conjugate (ATH). Therefore, the ATH is devoid of low molecular weight heparin chains conjugated to the AT.

Low molecular weight heparin chains can be removed from commercially available heparin prior to reacting the heparin with AT to form ATH. This produces ATH that is compositionally different from ATH formed from unfractionated heparin without removing the low molecular weight heparin before reaction with AT. Additionally, forming ATH from unfractionated heparin and then subsequently removing low molecular weight ATH does not produce the same product as the ATH of the present disclosure. Without being bound to any particular theory, it is believed that low molecular weight heparin chains (such as less than 3,000 Daltons or less than 5,000 Daltons) compete with longer chain heparins for conjugating to AT. The very low molecular weight heparin chains have a high proportion of aldose termini which react with the AT. Therefore, the very low molecular weight heparin chains tend to conjugate with AT more quickly, out-competing the higher molecular weight heparin chains. However, once the very low molecular weight heparin chains are bonded to the AT, the chains do not contain sufficient sites or length for binding thrombin and Factor Xa, an enzyme involved in the coagulation cascade. The inhibitory activity against factor Xa and thrombin drops dramatically in the lowest molecular weight range of heparin molecules. Thus, the ATH formed from these very low molecular weight heparin chains has essentially zero activity for preventing thrombogenesis. Although commercial heparin contains a relatively small percentage of heparin chains below 5,000 Daltons, these very low molecular weight heparin chains have such a high reactivity with AT so that a significant amount of the ATH formed contains the very low molecular weight heparin chains.

If the very low molecular weight heparin is not removed first, prior to conjugation, then a greater proportion of reactive termini in this population versus that of the higher molecular weight heparin will tend to outcompete the other heparin molecules to a varying degree across the entire molecular weight spectrum (as the proportion of aldose termini varies continually across the whole molecular weight range of heparin). This can have adverse effects on the final ATH. First, the ATH will contain a significant population of ATH molecules containing very small heparin chains with no activity. Second, the remaining ATH molecules (outside of this very low molecular weight range of ATH) will contain a population of heparin that has a reduced proportion of heparin chains in discrete molecular weight ranges that had fewer aldose termini to compete with the inactive low molecular weight heparin chains. This low aldose type heparin tends to be in the much longer chains but is not entirely defined by a straight relationship between heparin chain length and aldose termini required for linkage to AT.

Furthermore, heparin with at least 18 monosaccharide units can also be more effective at inhibiting thrombin. At least 18 monosaccharide units are used to bind both antithrombin and thrombin. The mechanism by which heparin binds antithrombin and thrombin is referred to as the template or bridging mechanism. Heparin can exert its effect via conformational activation by binding to AT and allosterically converting the AT into a structural form that is much more reactive towards coagulation proteases. Alternatively, heparin may act as a template through binding to both inhibitor and enzyme, thus localizing the molecules for reaction. In this mechanism, conformational activation of AT by heparin occurs but additional reaction rate enhancement is gained by simultaneous binding of heparin to the enzyme, thus assisting approach of the coagulation factor towards the activated inhibitor. The particular minimum chain length of 18 monosaccharides may explain why there is a very abrupt drop in activity against thrombin within the low molecular weight fraction of heparin. From the structure for a monosulfated uronic acid-disulfated glucosamine heparin disaccharide, that is without the sodium or other ions found in a salt form, the MW of an 18 saccharide (9 disaccharide) chain would be about 4500 Daltons.

Somewhat lower molecular weight heparin chains may be useful for inhibiting Factor Xa. A particular pentasaccharide sequence in heparin can bind to AT and activate the AT for inhibiting Factor Xa. The particular pentasaccharide sequence has been made available on its own as the pharmaceutical "Fondaparinux," but the sequence can occur in heparin chains as well. The sequence of monosaccharides is shown in Formula I:

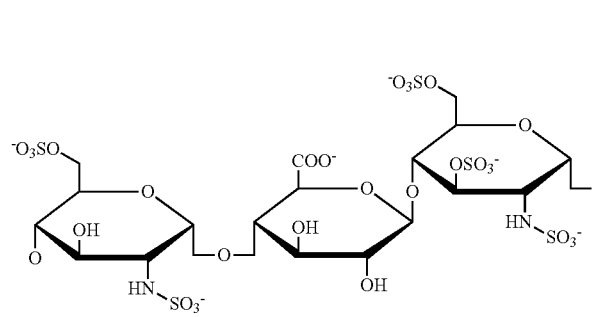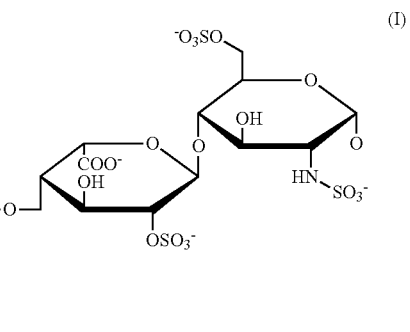

Thus, heparin chains with less than 18 monosaccharides that contain this pentasaccharide sequence may be able to activate AT to inhibit Factor Xa even though the chains are not long enough to bind to AT and thrombin.

The longest heparin chains can in some case have the highest inhibitory activity. However, some mid-range and lower molecular weight heparin chains can have significantly less undesirable binding to other plasma proteins and platelets. Therefore, these mid-range heparin chains can be more selective for inhibiting thrombin and factor Xa without causing unwanted side effects such as platelet dysfunction from binding with platelets and binding other materials.

Isolating the higher molecular weight ATH after the conjugation to give very long chain ATH provides a less desirable and distinct product compared to the present technology which separates out (substantially or fully) the heparin prior to conjugation. For example, the proportion of 2-pentasaccharide high activity molecules in this subpopulation may be altered because of a differential ability of these high activity chains to compete with the very low molecular weight heparins for conjugation. Additionally, isolating the high molecular weight ATH after conjugation eliminates ATH molecules with mid-range and lower sized heparin chains that are also active and have other desirable characteristics such as reduced non-selective binding to plasma proteins and platelets.

Alternatively, attempts to react all aldose-terminating heparin chains with AT by increasing the ratio of AT to heparin in the reaction mixture are not likely to succeed because many experiments have shown that only up to 60 wt % conversion of AT into ATH is obtained even with the aldose containing heparin in several-fold excess and at highest practical concentrations. Reducing the proportion of heparin to AT even more will only decrease the ATH yield further without any promise that all of the active longer chains will be incorporated into the product.

In some embodiments, a composition for preventing thrombogenesis can contain ATH formed from commercial heparin from which substantially all of the heparin chains with a molecular weight less than 3,000 Daltons have been removed (e.g., at least 98 wt % of remaining heparin chains can have a molecular weight greater than 3,000 Daltons). In other embodiments, heparin chains with a molecular weight less than 5,000 Daltons can be substantially removed or removed. Thus, the ATH product can contain heparin chains that range in molecular weight from 3,000 Daltons (or 5,000 Daltons) up to the highest molecular weights contained in the commercial heparin. In certain examples this range of molecular weights can be from 3,000 Daltons to 50,000 Daltons, or from 5,000 Daltons to 50,000 Daltons. In additional examples, at least a portion of the heparin chains can be in a mid-molecular weight range. For example, at least a portion of the heparin chains in the ATH can have a molecular weight from 3,000 Daltons to 30,000 Daltons, from 3,000 Daltons to 20,000 Daltons, from 3,000 Daltons to 15,000 Daltons, from 3,000 Daltons to 10,000 Daltons, from 5,000 Daltons to 30,000 Daltons, from 5,000 Daltons to 20,000 Daltons, from 5,000 Daltons to 15,000 Daltons, or from 5,000 Daltons to 10,000 Daltons. Thus, the ATH can be substantially devoid or devoid of heparin chains with a molecular weight below 3,000 Daltons or 5,000 Daltons.

Commercial heparin can typically contain a range of heparin chains with molecular weights ranging from 1,000 Daltons or less to 50,000 Daltons or more. The lowest molecular weight fraction, such as the chains with molecular weights below 3,000 or 5,000 Daltons, can be removed by any suitable method. Non-limiting examples of methods for removing the low molecular weight chains include dialysis, diafiltration, gel filtration and electrophoresis. Dialysis or diafiltration can be performed under high salt conditions. For example, high salt conditions for dialysis or diafiltration can include salt concentrations from about 1 M NaCl to about 4 M NaCl. Salts other than NaCl can also be used. The high salt concentration can assist movement of the small chains through membranes having appropriate pore sizes. Gel filtration can be performed using a suitable media for separating molecules by size. In one particular example, gel filtration can be performed on Sephadex® G-200, which is a gel media for separating molecules with molecular weights in the range of 1,000 to 200,000 Daltons. Commercial heparin can be gel filtered on a column of gel media, and a series of fractions can be eluted with the first fractions containing the highest molecular weight chains and the subsequent fractions containing progressively lower molecular weights. The molecular weights of heparin in each fraction can be determined, and the fractions having the desired molecular weights can be pooled. Using this method, fractions containing heparin with molecular weights below the threshold of 3,000 or 5,000 Daltons can be excluded. If desired, heparin chains above a certain threshold can also be excluded. For example, fractions containing heparin above 50,000 Daltons, 30,000 Daltons, 20,000 Daltons, 15,000 Daltons, or 10,000 Daltons can be excluded if desired. The pooled fractions having the desired range of molecular weights can then be used to synthesize ATH.

It should be noted that the methods of removing the very low molecular weight heparin chains described above are only exemplary and should not be considered limiting. Any method of processing commercial heparin to remove heparin chains below a certain threshold molecular weight can be used in the present disclosure.

In various embodiments of the present disclosure, the treatments and methods described herein can be performed using ATH having low molecular weight heparin removed, or alternatively, using ATH formed from unfractionated heparin.

ATH can be formed by conjugating AT with the heparin that is now devoid of very low molecular weight chains. Exemplary methods of conjugating heparin with AT are disclosed in U.S. Pat. No. 7,045,585, which is incorporated herein by reference. These methods can be applied to forming ATH using heparin from which the very low molecular weight chains have been removed, as described herein. Heparin can be conjugated with AT through a simple one-step process, which provides for direct covalent attachment of the amine of an amine containing moiety (such as, but not limited to, amine containing oligo(poly)saccharides, amine containing lipids, proteins, nucleic acids and any amine containing xenobiotics) to a terminal aldose residue of a heparin chain. For forming ATH, the amine containing moiety is present in the AT, although other proteins can be conjugated using the same methods. The mild non-destructive methods provided herein allow for maximal retention of biological activity of the protein and allow direct linkage of the protein without the need for intermediate spacer groups.

In one embodiment, heparin is incubated with AT at a pH suitable for imine formation between the amine and the terminal aldose or ketose residue of the heparin. Terminal aldose and ketose residues generally exist in an equilibrium between the ring closed cyclic hemiacetal or hemiketal form and the corresponding ring opened aldehyde or ketone equivalents. Generally, amines are capable of reacting with the ring opened form to produce an imine (Schiff base). Typically, the aldoses are more reactive because the corresponding aldehydes of the ring open form are more reactive towards amines. Therefore, covalent conjugate formation between amines and terminal aldose residues of heparin provides a method of attaching the AT containing an amine to the heparin.

The reaction is typically carried out at a pH of about 4.5 to about 9, and more typically at about 5 to about 8, and even more typically about 7 to about 8. The reaction is generally done in aqueous media. However, organic media, especially polar hydrophilic organic solvents such as alcohols, ethers and formamides and the like may be employed in proportions of up to about 40% to increase solubility or reactivity of the reactants, if necessary. Non-nucleophilic buffers such as phosphate, acetate, bicarbonate and the like may also be employed.

In some cases the imines formed by condensation of the amines of the AT with the terminal aldose residues of the heparin are reduced to the corresponding amines. This reduction may be accomplished concurrently with imine formation or subsequently. A wide array of reducing agents may be used, such as hydride reducing agents including sodium borohydride or sodium cyanoborohydride. In one example, any reducing agent that does not reduce disulfide bonds can be used.

Alternatively, if reduction of the intermediate imine is not desired, the imine may be incubated for a sufficient period of time, typically about 1 day to 1 month, more typically about 3 days to 2 weeks, to allow Amadori rearrangement of the intermediate imine. The terminal aldose residues of the heparins conjugated by the methods provided by this disclosure frequently possess C2 hydroxy groups on the terminal aldose residue, i.e., a 2-hydroxy carbonyl moiety which is converted to a 2-hydroxy imine by condensation with the amine of the AT being conjugated to the heparin. In the Amadori rearrangement, which is particularly common in carbohydrates, the α-hydroxy imine (imine at C1, hydroxy at C2) formed by the initial condensation may rearrange to form an α-keto amine by enolization and re-protonation (keto at C2, amine at C1)). The resulting α-carbonyl amine is thermodynamically favored over the precursor α-hydroxy imine, thus providing a stable adduct with minimal disruption of the heparin chain. Thus, in this embodiment, the technology provides a heparin chain covalently conjugated at the C1 of the terminal aldose residue of the heparin to an amine containing AT via an amine linkage. If desired, the resulting conjugate may be reduced or labelled by reduction of the C2 carbonyl group with a labelling reagent, such a radiolabel (e.g., $NaB^3H_4$), or conjugated to a second species, such as a fluorescent label.

Although the above description focuses on heparin and AT, a variety of different amine containing species may be conjugated to a variety of glycosaminoglycans by the methods disclosed herein. The primary amine may be on a small molecule, such as, for example, a drug or fluorescent or chromophoric label or a macromolecule such as, for example, a protein (antibodies, enzymes, receptors, growth factors and the like), a polynucleotide (DNA, RNA and mixed polymers thereof), a lipid or a polysaccharide. Generally, when proteins are being conjugated to glycosaminoglycans, linkage will occur through the ε-amino groups of lysine residues. Alternatively, linkage may also be accomplished via the α-amino group of the N-terminal amino acid residue. In addition, many other methods can be used that are known to those of skill in the art to introduce an amine functionality into a macromolecule.

In particular, the present technology can be applied to a variety of other therapeutically useful proteins where longer half-life and blood coagulation considerations can be useful. These include blood enzymes, antibodies, hormones and the like as well as related plasminogen activators such as tissue plasminogen activator, streptokinase and derivatives thereof. In particular, this technology provides conjugates of heparin or dermatan sulfate with antithrombin, heparin cofactor II (HCII) or analogs of heparin cofactor II.

The methods of the present disclosure provide glycosaminoglycan conjugates with maximal retention of biological activity. In particular, conjugates of heparin or dermatan sulfate with either AT or HCII are provided which possess >60 wt %, typically >90 wt %, more typically >95 wt %, and most typically >98 wt % of intact unconjugated heparin antithrombin activity. The methods of the present technology provide intact heparin molecules conjugated to antithrombin or heparin cofactor II. Thus, loss of biological activity associated with fragmentation or other modification of heparin prior to conjugation is avoided. The heparin conjugates of this technology retain their anticoagulant activity because of their preparation from intact heparin. Therefore, the methods disclosed herein can be used to prepare active heparin conjugates by first attaching linking groups and spacers to the species sought to be conjugated to heparin (or whatever the glycosaminoglycan being used) and subsequently attaching it to heparin. Numerous methods of incorporating reactive amino groups into other molecules and solid supports are described in the ImmunoTechnology Catalog and Handbook, Pierce Chemical Company (1990), incorporated by reference. Thereby, any species possessing reactive amino groups or capable of being modified to contain such amino groups, by any method presently known or that becomes known in the future, may be covalently conjugated to glycosaminoglycans, such as heparin, by the methods disclosed herein and all such conjugates are contemplated by this disclosure.

As described above, the present technology takes advantage of the fact that native (isolated from intestinal mucosa) heparin, as well as dermatan sulfate, already contains molecules with aldose termini which would exist in an equilibrium between hemiacetal and aldehyde forms. Thus, heparin or dermatan sulfate can be conjugated to antithrombin serpins by reduction of the single Schiff base formed spontaneously between the aldose terminus aldehyde on heparin or dermatan sulfate and an amino on the serpin. The heparin or dermatan sulfate is unmodified (unreduced in activities) prior to conjugation and is linked at one specific site at one end of the molecule without any unblocked activation groups or crosslinking of the serpin.

In another aspect of this disclosure, covalent complexes can be produced by simply mixing heparin and AT in buffer and allowing a keto-amine to spontaneously form by an Amadori rearrangement between the heparin aldose terminus and an AT amino group. Thus, this technology provides methods of using the Amadori rearrangement to prepare conjugates of glycosaminoglycans to amine containing species, particularly proteins. This is a particularly mild and simple method of conjugation, which minimizes the modification of the glycosaminoglycan, thus maximizing the retention of its biological activity.

Another aspect of this technology provides covalent conjugates of glycosaminoglycans, particularly of heparin, end-labelled with an amine containing species at the terminal aldose residue of the glycosaminoglycan. For example, heparin and AT can be linked directly together so that the active pentasaccharide sequence for AT on the heparin is in close proximity for binding. This is one of the fundamental reasons for making a covalent heparin-AT complex, as heparin accelerates inhibition through AT only if AT can bind the active sequence. It is notable that ATH has the unique property that the H (heparin) in the conjugate stoichiometrically activates the endogenous AT while catalytically activating exogenous AT. Typically, one amine containing species will be attached to each glycosaminoglycan. However, it will be apparent that the ratio of amine containing species to glycosaminoglycan may be reduced below one by adjusting the molar ratios of the reactants or the time of the reaction.

Glycosaminoglycans are available in a variety of forms and molecular weights. For example, heparin is a mucopolysaccharide, isolated from pig intestine or bovine lung and is heterogenous with respect to molecular size and chemical structure. It consists primarily of (1-4) linked 2-amino-2-dexoxy-α-D-gluopyranosyl, and α-L-idopyranosyluronic acid residues with a relatively small amount of β-D-glucopyranosyluronic acid residues. The hydroxyl and amine groups are derivatized to varying degrees by sulfation and acetylation.

Heparin molecules can also be classified on the basis of their pentasaccharide content. About one third of heparin contains chains with one copy of the unique pentasaccharide with high affinity for AT, whereas a much smaller proportion (estimated at about 1% of total heparin) consists of chains which contain more than one copy of the high affinity pentasaccharide. The remainder (approximately 66%) of the heparin does not contain the pentasaccharide. Thus, so called "standard heparin" constitutes a mixture of the three species, "low affinity" heparin that lacks a copy of the pentasaccharide, "high affinity" heparin that is enriched for species containing at least one copy of the pentasaccharide, and "very high affinity" heparin that refers to the approximately 1% of molecules that contain more than one copy of the pentasaccharide. These three species can be separated from each other using routine chromatographic methods, such as chromatography over an antithrombin affinity column.

One advantage of forming a conjugate between heparin and a species containing at least one primary amino group (e.g., AT) using the slow glycation process disclosed herein, is the apparent selection for heparin chains having two pentasaccharides. Thus, for example, ATH prepared by the method of this disclosure appears to be enriched for heparin species containing two pentasaccharides. When standard heparin (containing approximately 1% of two-pentasaccharide heparin) is used as a starting material, usually more than 10% of the resulting ATH comprises two-pentasaccharide heparin, more often more than about 20%, frequently more than 35%, and often more than about 50% of the ATH comprises two-pentasaccharide heparin.

This enrichment may account for several useful properties of ATH. The ATH of the present technology activates the AT to which it is conjugated, in a stoichiometric fashion, but activates exogenous AT in a catalytic fashion. Thus, the heparin within the ATH complex acts catalytically both when ATH is administered as systemic anticoagulant and when ATH is used to coat surfaces to render them non-thrombogenic. The method of the technology produces an ATH complex with very high specific anti-factor IIa activity. In addition, the second pentasaccharide chain in the ATH complex can interact with exogenous AT molecules, thereby allowing the conjugated heparin to have catalytic activity. Moreover, the heparin in the ATH complex can be orientated in such a way that the pentasaccharide is available to bind and activate circulating AT molecules when the ATH complex is bound to a prosthetic surface.

It will be appreciated that a heparin conjugate of interest (e.g., ATH) can also be produced by incubating a species containing at least one primary amino group (e.g., AT) with purified very high affinity heparin (i.e., containing two pentasaccharide groups) or a fraction enriched for very high affinity heparin.

Though this technology has been illustrated primarily with respect to heparin, it is apparent that all glycosaminoglycans, irrespective of their molecular weight and derivatization, may be conjugated by the methods disclosed herein, provided they possess a terminal aldose residue. Conjugates of all such glycosaminoglycans and their preparation by the methods herein are within the scope of this disclosure. For example, conjugates of heparin derivatized with phosphates, sulfonates and the like as well as glycosaminoglycans with molecular weights lower or higher than the molecular weights of heparin are within the scope of this disclosure.

In a further aspect of the present disclosure, a method of making a composition for preventing thrombogenesis can include conjugating AT with heparin outside a body of a subject to form an antithrombin-heparin conjugate, wherein the amount of antithrombin yielded in the antithrombin-heparin conjugate is greater than 60 wt %, greater than 65 wt %, greater than 75 wt %, greater than 85 wt %, greater than 90 wt %, greater than 95 wt %, or greater than 99 wt % based on the starting antithrombin used in the synthesis. The yield can be increased by various methods. In one example, AT can be conjugated to heparin by the methods described above. Following the conjugation, any unbound AT can be recycled and used in another conjugation reaction with heparin. After each step of incubating AT with heparin, the unbound AT can be recycled and used to make additional ATH.

In another example, the yield of ATH can be increased by using an Amadori rearrangement catalyst. Non-limiting examples of catalysts that can increase the rate of Amadori rearrangement include 2-hydroxypyridine, tertiary amine salts, ethyl malonate, phenylacetone, acetic acid, as well as other acids. In a particular example, AT and heparin can be reacted in the presence of 2-hydroxypyridine while being heated in water or very amphiphilic solvents such as formamide. In further examples, AT and heparin can be reacted in the presence of trimethylamine or trimethylamine salts.

The rate of the Amadori rearrangement can also be increased by Amadori rearrangement accelerating solvent systems. Non-limiting examples of solvents include mixtures of water with formamide, dimethylformamide, dioxane, ethanol, dimethylsulfoxide, pyridine, acetic acid, trimethylamine, triethylamine, acetonitrile, and combinations thereof. Heparin and AT can be reacted in these solvent systems to accelerate the Amadori rearrangement to form ATH.

An additional method for increasing the rate of conjugating the heparin aldose to an amine-containing molecule involves using a linking agent. The linking agent can be a heterobifunctional agent, with a group reactive toward the aldose of heparin at one end and a different group at the other end that can be used for linking either to AT or to a secondary linking agent that can then be linked to AT. In one particular example, the linking agent can contain hydrazine at one end and an amino group at the other end, such as 2-aminoethylhydrazine. This linking agent can be reacted with heparin to form a hydrazone with the aldose aldehyde of the heparin. The product can be dialyzed or diafiltered with membranes that allow heparin chains less than 3,000 or 5,000 Daltons in molecular weight to be removed along with any unreacted linking agent. The heparin-hydrazone product can then be reacted with a large excess of a secondary linking agent. The secondary linking agent can be a homobifuntional reagent possessing activated carboxyl groups at each end, such as succinic acid di(N-hydroxysuccinimide) ester (prepared by esterifying succinic acid with N-hydroxysuccinimide using condensing agents such as carbonyldiimidazole or a carbodiimide) so that the amino group on the hydrazine linking agent reacts with just one of the activated carboxyls on the secondary linking agent. The reaction mixture can be dialyzed or diafiltered to remove unreacted secondary linking agent. At this point, the product is heparin modified with the amino-hydrazine linking agent as well as the secondary linking agent. This product can be incubated with AT in buffered $H_2O$ so that the amino group on the AT reacts with the second activated carboxyl group on the secondary linking agent to form an AT-Heparin conjugate, where the AT and heparin are linked by the linking agent and the secondary linking agent.

After forming ATH, the ATH can be lyophilized (freeze-dried) for storage. In one embodiment, the ATH can be prepared in a solution containing only water and then lyophilized. In another embodiment, the ATH can be prepared in a solution with water and alanine at a concentration of from 0.01-0.09 molar, and then lyophilized. In yet another embodiment, the ATH can be prepared in a solution containing water and mannitol, and then lyophilized. Each of these methods can be used independently, and each method can provide its own advantages. After lyophilization using any of these methods, the ATH can be reconstituted and retain a significant amount of its activity for inhibiting thrombin compared to its activity prior to lyophilization. In some cases, the ATH can retain at least 50%, at least 60%, at least 70%, at least 80%, at least 90%, at least 95%, or at least 98% of its activity for inhibiting thrombin. It has been found that using other methods of lyophilizing ATH, such as preparing the ATH in a solution containing greater than 1 molar salt before lyophilization, can destroy the activity of the ATH.

Whether the ATH has been lyophilized or not, the ATH can be prepared in an aqueous solution containing from 9-11 mg/mL of ATH with respect to the entire volume of the solution. It has been found that forming solutions with an ATH concentration higher than 11 mg/mL can lead to aggregation of ATH that is difficult or impossible to reverse. However, stable aqueous solutions can be prepared with ATH concentrations of 9-11 mg/ml. This solution can be formulated for administration to a subject for treatment of any of the conditions described herein. The solution can also include a variety of additives as are suitable for administering to a subject.

In clinical practice, the heparin conjugates of the present technology may be used generally in the same manner and in the same form of pharmaceutical preparation as commercially available heparin for clinical use. Thus, the heparin conjugates provided by the present technology may be incorporated into aqueous solutions for injection (intravenous, subcutaneous and the like) or intravenous infusion or into ointment preparations for administration via the skin and mucous membranes. Any form of therapy, both prophylactic and curative, either currently known or available in the future, for which heparin therapy is indicated may be practiced with the heparin conjugates provided by this technology.

The heparin conjugates of this technology find particular utility in the treatment of neonatal and adult respiratory distress syndrome (RDS). In contrast to the use of noncovalent heparin-AT complexes, the use of the covalent heparin conjugates of the present technology prevents loss of heparin in the lung space by dissociation from AT. In this case, a solution of covalent complex in a physiologic buffer can be delivered as an atomized spray down the airway into the lung via a catheter or puffer. Due to its large size, ATH will remain in the alveoli for a longer period of time. ATH is also useful for treatment of idiopathic pulmonary fibrosis.

Long term use in the circulation can be carried out by either intravenous or subcutaneous injection of the complex in a physiologic buffer. The covalent conjugates of this technology may also be used in the treatment of acquired AT deficient states characterized by thrombotic complications such as cardiopulmonary bypass, extracorporeal molecular oxygenation, etc. because a longer half-life of the covalent complex allows for fewer treatments and less monitoring. Additionally, this disclosure provides for prophylactic treatment of adult patients at risk for deep vein thrombosis.

The ATH conjugate of this technology has numerous advantages over uncomplexed AT and standard heparin. Since the AT is covalently linked to the heparin, non-specific binding of ATH to plasma proteins will be less than occurs with standard heparin, resulting in less inter-individual variation in dose response to ATH than there is to standard heparin. The longer half-life of ATH after intravenous injection in humans means that a sustained anticoagulant effect may be obtained by administering ATH less frequently than is required for uncomplexed AT and standard heparin. ATH is a much more effective inactivator of thrombin and factor Xa than AT, and can be effective when used in much lower concentrations than AT in patients with AT deficiency. In addition, ATH can access and inhibit thrombin bound to fibrin. Finally, when linked (e.g., covalently linked) to prosthetic surfaces (e.g., endovascular grafts), ATH has shown much greater antithrombotic activity in vivo than covalently linked AT, covalently linked heparin, or covalently linked hirudin.

Premature infants have a high incidence of respiratory distress syndrome (RDS), a severe lung disease requiring treatment with assisted ventilation. Long term assisted ventilation leads to the onset of bronchopulmonary dysplasia (BPD) as a result of lung injury which allows plasma coagulation proteins to move into the alveolar spaces of the lung. This results in the generation of thrombin and subsequently fibrin. The widespread presence of fibrin within the lung tissue and airspaces is consistently observed in infants dying of RDS. This fibrin gel within the airspace impairs fluid transport out of the lung airspaces resulting in persistent and worsening pulmonary edema. The present technology provides for treatment of such fibrin-mediated diseases in lung tissue by preventing intra-alveolar fibrin formation by maintaining an "anti-thrombotic environment" and/or enhancing fibrinolysis within lung tissue, thereby decreasing the fibrin load in the air spaces of the lung.

The heparin conjugates can be delivered directly to the airspaces of the lung via the airway prophylactically (before the baby takes its first breath). This ensures that the antithrombotic agent is available directly at the site of potential fibrin deposition and that the bleeding risk associated with systemic antithrombotic therapies is avoided. In addition, the antithrombotic agent will already be present in the lung prior to the start of the ventilatory support which is associated with the initial injury, i.e., unlike systemic antithrombin administration where crossing of the administered drug to the lung airspace does not occur until after lung injury. Since heparin is covalently attached to AT it will remain in the lung airspaces. It can also be an adjunctive therapy to the surfactants currently administered to prevent RDS and BPD. By "lung surfactant" is meant the soap-like substance normally present in the lung's airspaces whose main role is to prevent collapse of the airspace, as well as assist gas transfer. The conjugates can also be delivered repeatedly via the endotracheal tube or as an inhaled aerosol. Adjunctive therapy can also be practiced with asthma medications by inhaler (e.g., anti-inflammatory steroids such as beclomethasone dipropionate), other anti-asthmatics such as cromolyn sodium (disodium salt of 1,3-bis(2-carboxychromon-5-yloxy)-2-hydroxypropane, ("INTAL") and bronchodilators such as albuterol sulfate.

A variety of other diseases associated with elevated thrombin activity and/or fibrin deposition can be treated by administration of the conjugates of this disclosure. The inflammatory processes involved in adult respiratory distress syndrome are fundamentally similar to neonatal RDS and can be treated by the antithrombotic therapy described. Spontaneous lung fibrosis has also been shown to have activation of the coagulation/fibrinolytic cascades in the lung airspaces. Fibrotic disease of the lung is often a side effect associated with cancer chemotherapy and the RDS antithrombotic administration of the covalent heparin conjugates of this technology can be administered prophylactically prior to cancer chemotherapy to prevent lung fibrosis. Administration is repeated after chemotherapy in order to ensure no fibrin formation. A decrease in antithrombin activity and an increase in thrombin activity in sepsis is also well documented. Sepsis is the most common risk factor for developing adult RDS. Thus, the heparin conjugates of this disclosure can be used to reduce the mortality associated with septic shock.

The conjugates of this disclosure can be administered at a therapeutically effective dosage, i.e., that amount which, when administered to a mammal in need thereof, is sufficient to effect treatment, as described above (for example, to reduce or otherwise treat thrombosis in the mammal, or to inactivate clot-bound thrombin, or to inhibit thrombus accretion). Administration of the active compounds and salts described herein can be via any of the accepted modes of administration for agents that serve similar utilities.

Generally, an acceptable daily dose is of about 0.001 to 50 mg per kilogram body weight of the recipient per day, about 0.05 to 25 mg per kilogram body weight per day, or about 0.01 to 10 mg per kilogram body weight per day. Thus, for administration to a 70 kg person, the dosage range can be about 0.07 mg to 3.5 g per day, about 3.5 mg to 1.75 g per day, or about 0.7 mg to 0.7 g per day depending upon the individuals and disease state being treated. In the case of ATH, the long half-life allows the compound to be administered less frequently than standard heparin (e.g., once or twice weekly).

Administration can be via any accepted systemic or local route, for example, via parenteral, intravenous, nasal, bronchial inhalation (i.e., aerosol formulation), transdermal or topical routes, in the form of solid, semi-solid or liquid dosage forms, such as for example, tablets, suppositories, pills, capsules, powders, solutions, suspensions, aerosols, emulsions or the like, such as in unit dosage forms suitable for simple administration of precise dosages. Usually, aqueous formulations can be used. The conjugate can be formulated in a non-toxic, inert, pharmaceutically acceptable carrier medium, at a pH of about 3-8 or at a pH of about 6-8. Generally, the aqueous formulation can be compatible with the culture or perfusion medium. The compositions will include a conventional pharmaceutical carrier or excipient and a conjugate of the glycosaminoglycan, and in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose or mannitol, and glycols are examples of suitable liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in Remington's Pharmaceutical Sciences by E. W. Martin (1985).

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this disclosure can be administered as a pharmaceutical composition which comprises a pharmaceutical excipient in combination with ATH. The level of the ATH in a formulation can vary within the full range employed by those skilled in the art, e.g., from about 0.01 percent weight (% w) to about 99.99% w of the drug based on the total formulation and about 0.01% w to 99.99% w excipient. In one example, the formulation can be about 3.5 to 60% by weight of the pharmaceutically active compound, with the rest being suitable pharmaceutical excipients.

The present invention also extends to treatments for various conditions using ATH. In some examples, this includes methods of treatment, compositions containing ATH, and medical devices comprising ATH. As described herein, ATH can provide several advantages over heparin. Heparinoid anticoagulants are commonly used to treat and prevent thrombotic disease. Heparinoids function by catalyzing the anticoagulant activity of the plasma protease inhibitor antithrombin. Unfractionated heparin (UFH) and its low molecular weight derivatives (LMWH) suffer from a number of shortcomings, including a short half-life, variable anticoagulant response, limited effectiveness at inhibiting thrombin (particularly clot-bound thrombin), induction of bleeding, and induction of thrombocytopenia.

ATH can solve many of these problems when used as a therapeutic agent. Compared to traditional heparinoids, ATH has an increased half-life, decreased binding to plasma proteins and endothelial cells, and increased antithrombotic efficacy in animal models without increased risk of bleeding. In vitro, ATH directly inhibits several coagulation factors, with significantly increased rates compared to non-covalent AT and UFH mixtures (AT+H). ATH is also more effective at inhibiting clot-bound thrombin compared to AT+H.

In some embodiments of the present invention, ATH can be used to form coatings on medical devices. In one embodiment, a method of coating a polymeric surface with an antithrombin-heparin conjugate can include contacting the polymeric surface with a solution of antithrombin-heparin conjugate such that the antithrombin-heparin conjugate directly coats the polyurethane surface without linking groups between the antithrombin-heparin conjugate and the polymeric surface.

Known methods of covalently attaching molecules to polymeric surfaces can be used to attach ATH to a polymeric surface of a medical device. For example, the polymeric surface can first be activated by treatment with an oxidant or reductant, then a linking group can be attached to the activated surface. The ATH can then be linked to the monomer. In one example, a polyurethane surface is activated by reaction with sodium hypochlorite or lithium aluminum hydride. Then, allyl glycidyl ether is grafted onto the surface to act as a linking group. The ATH is then linked to the linking group.

Although ATH can be attached to surfaces using linking groups in this way, it has been found that, surprisingly, ATH can also bond with a polymeric surface directly, without any linking group. Thus, the present invention provides for simple methods of coating polymeric surfaces with ATH without activating the polymeric surface or attaching a linking group to the surface. In some examples, a polymeric surface can simply be contacted with a solution of ATH by dipping or other methods. The ATH can attach directly to the surface and remain attached even after washing with detergents. This method can be useful for coating medical devices that come in contact with blood to reduce the thrombogenicity of the medical devices.

The polymeric surface can be composed of any polymer used in manufacturing medical devices. In some embodiments, the polymeric surface can be a polyurethane surface, a polyethylene surface, a polypropylene surface, a polytetrafluoroethylene surface, a polydimethylsiloxane surface, and ethylene-acrylic acid copolymer surface, a Dacron surface, a polyester-polyurethane surface, a polyurethane-polycarbonate surface, a polyvinyl chloride surface, a silicone surface, a latex rubber surface, a nitinol surface, a Nylon surface, a polyethylene terephthalate surface, a polystyrene surface, or combinations thereof. In other embodiments, the polymeric surface can include loplex materials and other hydrogels such as those based on 2-hydroxyethyl methacrylate or acrylamide, and poly ether polyurethane ureas (PEUU) including Biomer (Ethicon Corp.) and Avcothane (Avco-Everrett Laboratories).

The polymeric surface can be a part of a medical device that comes in contact with blood. In some embodiments, the medical device can be an intravenous catheter, an intra-arterial catheter, a peripherally inserted central catheter, a central catheter, a Swan-Ganz catheter, a coronary stent, an arteriovenous shunt, an inferior vena cava filter, a dialysis catheter, a dialysis blood circuit line, a dialysis membrane, an extracorporeal membrane oxygenation line, an extracorporeal membrane oxygenation membrane, an in vivo prosthetic, a pacemaker lead, a suture, a blood filter, a mechanical valve, an artificial organ, or a blood storage container. Any internal or external medical device that comes in contact with blood and for which it would be desirable to reduce blood coagulation can potentially be coated with ATH.

In a particular embodiment, the medical device can be a catheter with an ATH coating. Catheters often fail due to surface-induced thrombosis. Coating of these devices with conventional anticoagulants like heparin can provide limited improvement, but occlusion of the device by clots remains a significant problem. ATH-coated devices display vastly superior antithrombotic properties and can be used without any thrombotic occlusion occurring.

In one example, a catheter can be coated with ATH by dipping the catheter in a solution of ATH. The interior of the catheter can be contacted with the ATH solution by drawing the solution up into the lumen of the catheter using a syringe. The catheter can then be incubated for a period of time to allow ATH to bond to the polymeric surfaces of the catheter. This period time can be, for example, 0.1-48 hours, 1-48 hours, 1-24 hours, 2-8 hours, or another period of time sufficient for ATH to bond to the polymeric surface. The catheter can then be removed from the ATH solution, excess ATH solution can be allowed to drain from the catheter, and the remaining coating of ATH solution can dry. Drying can be for any period of time sufficient for the solvent to evaporate from the ATH solution coating the catheter. In one embodiment, the catheter can be dried in still, room temperature air. The drying time can be, for example, 1-48 hours, 1-24 hours, 1-8 hours, or 1-2 hours. In other embodiments, the catheter can be dried in flowing air from a blower, still or flowing heated air (such as air heated up to about 60° C.), still or flowing dehumidified air, still or flowing nitrogen, still or flowing noble gas, or a partial or full vacuum. The drying time can be less when flowing, dehumidified, or heated air or other gas is used. The drying time can also be substantially less when partial or full vacuum is used. For example, the drying time can be from 1 minute to 48 hours, 1 minute to 24 hours, 1 minute to 1 hour, 1-30 minutes, or another sufficient drying time. Once dried, the catheter can be are used in vitro or sterilized for use in medical applications. One method of sterilization can include placing the catheter in a sealed container with a gas permeable membrane and sterilizing the catheter and container by exposure to ethylene oxide.

Various methods of coating a catheter or other medical device with ATH can be used. For example, a medical device can be submerged in an ATH solution and incubated for a sufficient period of time to allow ATH to bond to surfaces of the medical device. In another example, a flow-through method can be used in which the medical device is contacted with a flowing ATH solution. In one particular example, the medical device can be a catheter and the ATH solution can flow around the catheter so that ATH solution flows past both the exterior and interior surfaces of the catheter. ATH solution can be continuously recycled and flowed through the catheter for a sufficient period of time for ATH to bond to the surfaces of the catheter.

Multiple medical devices can be coated simultaneously in a single batch of ATH solution. For example, a sufficient volume ATH solution can be prepared to submerge any number of medical devices for incubation in the solution. Additionally, the ATH solution can be used to coat multiple batches of medical devices in sequence. Because the coating of ATH formed on the medical device surface can be only about one molecule thick, most of the ATH in the solution remains in solution after coating a medical device. As an example, a layer of ATH one molecule thick can contain about 2 pmoles of ATH/cm$^2$ of surface. However, 100 mL of 1 mg ATH/mL solution contains a total of $1.69 \times 10^6$ pmoles ATH. Therefore, the solution contains enough ATH to form a one-molecule thick coating on many medical devices. In one embodiment, a batch of ATH solution can be prepared and then a plurality of medical devices can be submerged and incubated in the ATH solution. After incubation, the medical devices can be removed and excess ATH solution can be allowed to drain back into the batch of ATH solution. Then, the same batch of ATH solution can be re-used to coat another plurality of medical devices. This process can be repeated multiple times to coat a large number of medical devices with only a single batch of ATH solution. In some cases, the process can be repeated up to 5 times, up to 10 times, up to 20 times, or even up to 50 times before preparing a new batch of ATH solution.

In a continuous flow-through method, the ATH solution can potentially be recycled indefinitely so that all the ATH in the solution is eventually used. For example, the ATH solution can be recycled as a series of medical devices is coated in the solution. When the concentration of ATH in the ATH solution drops below a threshold value, such as 0.1 mg ATH/mL, 0.5 mg ATH/mL, 0.8 mg ATH/mL, or 0.9 mg ATH/mL, then additional ATH can be added to the solution in this example.

In a specific example, a group of 50 catheters can be coated with ATH. This can be accomplished by dip coating the catheters in 200 mL of 1 mg ATH/mL buffer solution to accommodate all 50 catheters at once. Alternatively, the catheters can be dip-coated 5 or 10 at a time using a single batch of ATH solution. Thus, the batch of ATH solution required can be reduced from 200 mL to 40 mL or 20 mL.

Catheters and other medical devices coated with ATH can remain patent for considerably longer than devices coated with heparin. For example, catheters coated with ATH can remain patent in a vein or artery for up to a year without using any anticoagulant. In some cases, a catheter coated with ATH can remain patent in a vein or artery for from 1 week to 1 year, from 1 month to 6 months, from 2 months to 6 months, or other extended lengths of time. In some cases a medical device coated with ATH can remain clot-free indefinitely or at least for duration of use of the device. Thus, it is not necessary to remove and replace the device in a patient due to clot formation. The increased ability of ATH may be at least partly due to the fact that ATH can be a substantially 100% active anticoagulant, whereas heparin can contain a large percentage of inactive heparin chains.

In a particular embodiment, lyophilization coating can be used to coat a polymeric surface of a medical device with ATH. The polymeric surface can be contacted with ATH solution in the absence of linking groups. Excess ATH solution can be allowed to drain off the polymeric surface. Then, solvent can be evaporated from the polymeric surface under at least partial vacuum. This can form a dry coating of ATH on the polymeric surface. In some cases, the lyophilized coating can have better uniformity compared to coatings from other coating methods.

Beyond coating catheters and other medical devices with ATH, the present invention also extends to flush and lock solutions for catheters. Standard practice for many institutions is to flush and lock catheters with a dilute heparin solution in order to prevent clotting, however there is no clear agreement in the literature on the efficacy of heparin flushing for keeping catheters patent. As an anticoagulant, heparin has a number of limitations, including its dependence on adequate plasma levels of antithrombin, and the fact that only one third of commercial heparin preparations have anticoagulant activity. The reliance of heparin function on antithrombin is a special concern in young children where neonates and, particularly, premature infants have significantly reduced plasma antithrombin concentrations compared to adults.

Heparin coatings are frequently used to make surfaces more anti-thrombogenic. However, these surfaces are not ideal due to leaching of the heparin from the surface, non-uniform substitution, and variable anticoagulant activities of the product. Since two-thirds of standard unfractionated heparin does not contain the pentasaccharide sequence required for anticoagulation, this limits the level of anticoagulant activity that can be attained on the modified surface. In addition, the non-anticoagulant heparin chains can still promote deposition of proteins onto the surface, which may enhance thrombus formation. These problems can be avoided by using ATH.

In one embodiment, a solution for flushing and locking an intravenous or intra-arterial catheter can include an antithrombin-heparin conjugate.

In another embodiment, a flush and lock system can include: an intravenous or intra-arterial catheter; a flush and lock solution configured to be flushed through the catheter, wherein the flush and lock solution comprises an antithrombin-heparin conjugate; and a syringe configured to inject the flush and lock solution into the catheter.

In yet another embodiment, a method of maintaining patency of a catheter can include: inserting a catheter into a vein or artery of a subject so that an interior opening of the catheter opens inside the vein or artery and an exterior opening of the catheter opens outside the subject; injecting a solution comprising an antithrombin-heparin conjugate into the catheter through the exterior opening of the catheter; and sealing the exterior opening of the catheter such that at least a portion of the solution comprising the antithrombin-heparin conjugate remains within the catheter.

When a flush and lock solution is used with a catheter in this way, the catheter remains in contact with the ATH solution after locking. While the catheter is in contact with the ATH solution, ATH can bond to the surfaces of the catheter as described above. Thus, every time the catheter is flushed and locked using an ATH solution, the catheter can become further coated by ATH. When the flush and lock solution is injected through the catheter, ATH can bond to both the interior surfaces and the tip of the catheter. This can prevent thrombus formation inside the lumen of the catheter as well as at the tip of the catheter.

The ATH can be present in the flush and lock solution in an amount from 0.01-10 mg ATH/mL, 0.1-1 mg ATH/mL, or another effective amount. Other components of the solution can include water, sodium chloride, and buffers.

Since the heparin moiety in ATH already has a permanently bound AT molecule, less of the heparin chain is fully available for interaction with plasma proteins and cell surfaces than heparin. ATH binds less to plasma proteins and endothelial surfaces (HUVEC monolayers) compared to heparin. If ATH coating does bind to platelets, unlike heparin coatings, the ATH does not activate the platelets. Therefore, catheters with the ATH coating remain free of thrombi when heparin-coated catheters would form thrombi and become occluded. Even when platelets were activated due to stasis or other biophysical phenomena, ATH is superior to heparin (UFH) in the inhibition of the prothrombinase complex and concomitant thrombin generation on activated platelet surfaces. Given ATH's massive superiority as an anticoagulant relative to heparin, ATH can be much more effective at preventing initiation of coagulation. This is especially highlighted by the fact that, while heparin will fail to inhibit activated clotting factors within the tip of the catheter unless AT from the plasma also is present, ATH already has an extremely reactive AT molecule that can directly inhibit the clotting factors.

Additionally, ATH has much higher anti-Xa or anti-IIa activities, or catalysis of AT inhibition of factor Xa or thrombin. In fact, ATH has been found to be more than 4 times more potent in thrombin inhibition rate than the AT+H (heparin). A similar multi-fold higher anti-factor Xa catalytic activity for ATH versus heparin has been shown. ATH also can directly inhibit coagulation factors on its own without added AT, something that heparin cannot do. ATH can directly inhibit all the coagulation factors in the coagulation cascade. In contrast, the requirement for AT in the anticoagulant mechanism of heparin is very well documented. Unlike heparin, ATH can readily inhibit fibrin clot bound thrombin and inhibit factor Xa bound to phospholipid surface complexes such as prothrombinase. In fact, after ATH inhibits thrombin on the surface of clots, the ATH complex remains bound, converting the clot surface into an anticoagulant due to ATH's active heparin chain. These and other advantages make ATH useful for use in a flush and lock solution. Given ATH's much higher potency and other advantages, much lower concentrations of ATH in the lock solution will be needed compared to heparin solutions. For example, ATH can have at least 5 times more anti-Xa catalytic inhibitory activity compared to unfractionated heparin.

Citrate is sometimes used in flush and lock solutions. In comparison with citrate as a flush and lock solution, ATH can maintain patency of the catheter for a longer period of time at lower concentrations. Citrate prevents coagulation from occurring by chelating calcium in the blood. However, once citrate has bound to a calcium ion, it is no longer able to prevent coagulation by binding more calcium. Thus, once citrate is saturated, more calcium from the flowing blood will start the clotting cascade. On the other hand, ATH can continue to catalyze inhibition through the presence of AT in the plasma. Thus, ATH is never saturated or consumed and will continue to work.

ATH can inhibit thrombin directly (without added AT) 3.2 times faster than AT+heparin. ATH can inhibit factor VIIa complexes with tissue factor 28 times faster than AT+heparin. Based on these differences, a 3.2×28=89.6 lower ATH concentration can give an equivalent speed of reaction for inhibiting the coagulation cascade compared to heparin. Thus, the concentration of ATH can be at least 89.6 times lower than the concentration of heparin used in flush and lock solutions, even without considering the non-covalent coating of the catheter surface with ATH that will occur from presence of the ATH lock solution.

Current flush and lock solutions containing heparin result in 20% of central venous catheters becoming blocked and requiring replacement. If ATH is used in the flush and lock solution, these 20% of CVCs can maintain patency without needing replacement.

Replacements of catheters average 10,000 units per day in the US alone due to complications. Using ATH flush and lock solutions can reduce the number of catheter replacements required. This would decrease replacement costs, increase patient quality of life (less in-patient hospital time), prevent loss of days of treatment (such as cancer therapy on hold while waiting for a replacement CVC surgery to be scheduled), reduce surgical costs, and increase physician time to serve other patients.

In one example, ATH was used to permanently coat the surface of both stents and CVCs, which were then tested in animal models. The ATH-coated stents and CVCs showed significantly reduced clot formation compared to stents and CVCs coated with heparin and uncoated stents and CVCs.

Since it is not feasible for every different type and brand of CVC available to be coated with an anticoagulant, many institutions opt to flush catheters with an anticoagulant solution to prevent catheter-associated clotting. Using a flush and lock solution containing ATH can be more effective than using a heparin solution.

The present invention also extends to methods of treating conditions using ATH. ATH can be used to treat a variety of conditions that require inhibition of thrombogenesis. In some cases, ATH formed from unfractionated heparin can be used. In other cases, the ATH can be formed from heparin having low molecular weight heparin chains removed. In one embodiment, a method of treating a medical condition by inhibiting thrombogenesis in a mammal can include administering a dose of an antithrombin-heparin conjugate to the mammal, wherein at least 98% of heparin chains in the antithrombin-heparin conjugate have a molecular weight greater than 3,000 Daltons.

In some embodiments, ATH can be administered during invasive procedures to lower risk of thromboembolic complications. Invasive procedures, such as cardiopulmonary bypass (CPB), induce massive amounts of fibrin microemboli that can lodge in the brain, potentially leading to long-term cognitive dysfunction. ATH has been shown to significantly reduce High Intensity Transient Signals (HITS) in the carotid arteries of pigs undergoing cardiopulmonary bypass (CPB). Reduction of HITS may indicate a lower risk of thromboembolic complications during CPB and reduction in related neurological dysfunction post-surgery. Decreased HITS with ATH, compared to UFH+AT treatment, was achieved without a significant increase in bleeding (during or after CPB). ATH's superior ability to inhibit fibrin clot-bound thrombin and increased half-life relative to heparin may be responsible for its improved performance during CPB.

For prophylaxis (in prothrombotic patients without a clot needing treatment), ATH can be administered intravenously at a dosage ranging from 1 unit (in terms of anti-factor Xa activity) per kilogram (unit/kg) up to 1000 units/kg, with a typical dose being around 100 units/kg. If ATH has an anti-factor Xa activity of 130 units per milligram (units/mg), in terms of the AT component of ATH, then ATH dosages can range from about 0.008 mg up to about 8 mg, with a typical dose being around 0.8 mg. Dosages can also be determined in terms of mg of the heparin component of ATH using that the ratio of AT to heparin in ATH is 59 mg to 18 mg. Given ATH's longer intravenous half-life than heparin, ATH does not have to be administered as frequently. Thus, ATH could be given potentially from once per day up to once per week, with once per day being more common.

For resolution of a clot, ATH can be administered intravenously at a dosage ranging from 50 units (in terms of anti-factor Xa activity) per kilogram (units/kg) up to 2000 units/kg, with a typical dose being around 300 units/kg. If ATH has an anti-factor Xa activity of 130 units/mg (in terms of the AT component of ATH), then ATH dosages can range from about 0.4 mg up to about 15 mg, with a typical dose being around 2.3 mg. Given ATH's longer intravenous half-life than heparin, it does not have to be administered as frequently. Thus, ATH can be given from three times per day up to twice per week, with twice per day being more common. Once the clot is sufficiently diminished in size, treatment with ATH could be reduced in dose and frequency or discontinued.

For prophylactic administration during surgery, the dosage can depend on the type of surgery, with the more invasive procedures requiring higher ATH dosages. One of the most invasive, damaging surgeries is bypass surgery, which can be treated with ATH dosages (in terms of the AT component of ATH) from 1 to 6 mg/kg body weight. In some cases, an ATH dose of 3 mg/kg can be used during bypass surgery.

ATH can be delivered intravenously in the form of a solution containing simple iso-osmotic salts (such as 0.15 M NaCl) and physiologically acceptable buffers (such as HEPES at pH 7.4). No other protein, solubilizer, adjuvant or other additives are necessary but can optionally be included without significant deleterious effects on ATH function.

ATH can provide several advantages over heparin as a systemic anticoagulant. One problem associated with anticoagulants is bleeding. Bleeding can result from having too much anticoagulant in the blood. ATH has high anticoagulant activity but provides reduced bleeding compared to heparin. ATH also has other advantages over heparin. The AT in ATH is always activated and the rate determining step for heparin binding to AT is eliminated. Additionally, ATH directly inhibits activated coagulation factors such as thrombin with rates that are faster than heparin. Heparin can non-selectively bind to plasma and cell surface proteins in vivo, however, such non-selective binding is reduced with ATH. Further, ATH has a longer intravenous half-life than heparin. Finally, because the covalently-linked AT covers a significant portion of the ATH heparin chains, adverse interactions with platelets are reduced so that normal platelet function is maintained.

In another embodiment of the present invention, ATH can be used to treat ligneous conjunctivitis. A method of treating ligneous conjunctivitis in a mammal can include administering a dose of an antithrombin-heparin conjugate to an eye of the mammal.

Retinal venous occlusion due to ocular thrombosis is second only to diabetic retinopathy as a cause of vision impairment/loss from retinal vascular disease. In cases of plasminogen deficiency, ligneous conjunctivitis occurs with a fibrin membrane that covers the eye and obscures vision. Treatment of this thrombotic problem with plasminogen eye drops is modest due to inhibitors, and heparin eye drops are only partly effective due to variable presence of plasma antithrombin which heparin activates. ATH, unlike heparin, can be sequestered outside vascular spaces due to its large size. Also, ATH contains antithrombin so there is no reliance on the patient's system to provide this agent for the heparin anticoagulant to work. Thus, ATH can more effectively treat or prevent ocular thrombosis. In one example, ligneous conjunctivitis can be treated by administering daily eye drops containing ATH. ATH can be present in the eye drops at a concentration of 0.01-10 mg ATH/mL, 0.1-2 mg ATH/mL, or about 1 mg ATH/mL.

In another embodiment, a contact lens can be coated with ATH. The coated lens can then be worn on the eye of the patient to prevent ocular thrombosis.

Ligneous gingivitis is another condition related to plasminogen deficiency. ATH can be used to treat ligneous gingivitis. In one embodiment, a solution of ATH can be applied topically to the gums of a patient periodically to prevent fibrin formation in the gums.

In a further embodiment, ATH can be used to treat clotting disorders in the lungs. These can include respiratory distress syndrome (RDS) and acute lung injury, for example due to mechanical ventilation. Experiments in plasma on fetal distal lung epithelial (FDLE) cells have confirmed that ATH inhibits thrombin generation to a greater extent than equivalent doses of AT+UFH. This result shows that ATH can be used in prevention or treatment of intra-pulmonary coagulation. Intratracheal instillation of ATH can result in high anticoagulant activity in the lavage fluid for over 48 h, with no measurable activity systemically. Furthermore, ATH shows a tendency for selective proliferation of epithelium relative to fibroblasts. Thus, ATH has many of the characteristics necessary to alleviate major factors contributing to RDS, BPD and ventilation-induced pulmonary disease.

Neonatal and adult RDSs are characterized by leakage of plasma proteins of varying sizes into the airspace, which leads to interstitial and intra-alveolar thrombin generation with subsequent fibrin deposition. Strong and convincing evidence exists which clearly shows that coagulation leading to fibrin formation remains a key effector of lung injury. While absent in normal lung, the presence of fibrin in alveolar and interstitial compartments, during evolving diffuse alveolar damage, remains a marked characteristic of RDS. Since the introduction of surfactant therapy, the amount of fibrin directly observed in RDS patients has been reduced. However, since significant pulmonary thrombin activity is present in RDS, a paucity of cross-linked fibrin polymer may result from the fact that fibrin can clear from the lung quickly, as it does in several solid tumors. In fact, improved intrapulmonary fibrinolysis was shown to decrease fibrosis, further prooving the activity of fibrin in lung injury. Fibrin turnover in the lungs of RDS/BPD patients is locally disrupted, similar to that in acute RDS. In addition, fibrin deposition in the vasculature and pulmonary artery indicates the existence of vasoconstrictor mechanisms in the occurrence of increased pulmonary vascular resistance in RDS. Intra-alveolar fibrin deposition can have marked short and long term detrimental effects. Fibrin has been found to significantly impair surfactant function while fibrin degradation products have been linked to increased alveolar-capillary membrane permeability, thus further increasing plasma protein leakage into the airspace. Further evidence for activation of both the coagulant and fibrinolytic systems in the intra-alveolar space comes from the presence of both excess procoagulant and deficient fibrinolytic activities in broncho-alveolar lavage (BAL) fluid from RDS patients. Leakage of protein into the lungs has itself been associated with systemic activation of clotting, complement and polymorphonuclear lymphocytes. Fibroblasts are recruited by and proliferate in regions containing fibrin, leading to inappropriate remodeling of lung tissues, such as in fibrosis.

Fibrin is produced by thrombin cleavage of fibrinogen and is subsequently cross-linked. Initiation of coagulation in vivo has been shown to result primarily from appearance of active tissue factor (TF). Experiments investigating plasma thrombin generation on FDLE and fetal mixed lung cells have shown that procoagulant activity on lung epithelium or fibroblasts was due to VIIa activation by cell surface-bound TF. In fact, TF has been identified as the only activator of coagulation in cultured lung cancer cells. Further data have shown that premature newborns have TF-like thrombotic activity in the airspace. As a conjunctive feature, less developed lungs in the premature or fetal state are more permeable than adults to molecules entering the airspace from the systemic circulation. Thus, any pulmonary nidus for TF or other coagulant activity has more opportunity to contact factors of the coagulation cascade in the newborn, leading to fibrin deposition and complications found in RDS. Thus, the developmental state may influence the individual's susceptibility to prothrombotic insults. Other acute injury can arise from either biological or mechanical factors, which can be associated with coagulant pathology. For example, in the case of infection, there are significant evidences of pulmonary thrombin generation leading to deleterious outcomes. More recently, some physical mechanisms have been demonstrated to elicit thrombin generation and fibrin deposition. For some time, it has been known that patients (especially the young) requiring prolonged artificial, mechanical ventilation are observed to show evidence of damage to the lung tissue structures. Moreover, pulmonary and circulatory coagulation has been reported as a result of ventilation that can be blunted by administration of systemic AT. Further, ventilatory volutrauma has produced lung injury leading to deterioration in gas exchange that was improved with heparin. Again there is some inference that ventilation-induced damage associated with thrombosis is particularly significant in the young patients. Experiments have shown that high tidal volume ventilation in rats causes the release of functional TF into both the circulation and lung airway. TF and thrombin generation was only induced in newborn but not adult animals. This is consistent with other findings where TF-related coagulant activity was only expressed in adult humans with very high tidal volumes and no positive end-expiratory pressure. Appearance of peak thrombotic activity in newborn rats occurred after less than 15 min and persisted over hour long periods. Given the link between fibrin deposition and lung viability, control of TF procoagulant activity during acute (ventilatory) or chronic (BPD) injury may benefit resistance to pulmonary dysfunction and adverse tissue alteration. Interestingly, control of damage would also likely dampen lung tissue permeability that leads to the presence of fibrin and other plasma proteins which inhibit surfactant function. Indeed, an agent that could neutralize TF activity, block pathways leading to pulmonary cell dysfunction and moderate tissue remodeling during lung injury would greatly enhance the outcome in patients, particularly within the pediatric population.

ATH can address many of the limitations found in the treatment of pulmonary fibrin deposition by UFH. ATH has a direct non-catalytic inhibitory activity towards thrombin that is 4-10 fold faster than non-covalent AT+UFH mixtures. The rapid rate of direct thrombin inhibition by ATH would ensure neutralization of the low levels of thrombin involved in feedback activation of thrombin generation and would be present in edema fluid where concentrations of plasma AT may be insufficient for thrombin inhibition. In addition, ATH's potent ability to catalyze reaction of AT with thrombin would allow it to also utilize any AT diffusing into alveolar spaces. Apart from the rapid fluid phase thrombin inhibition, ATH can inhibit the fibrin-bound thrombin which is resistant to reaction with non-covalent AT-UFH. The inhibition of clot-bound thrombin contributes to the reduction of venous clots by ATH without a significant increase in hemorrhagic side-effects. On FDLE surfaces, ATH has proved to be vastly superior in the inhibition of plasma thrombin generation compared to similar doses of AT+UFH. Furthermore, comparison of ATH with unfractionated and low molecular weight heparins has shown that ATH can inhibit thrombin generation in either adult, child or newborn plasmas with greater potency. Intra-tracheal administration of ATH in rabbits and newborn rats demonstrated that high levels of anticoagulant activity can be detected in lavage fluid at least 2 to 4 days later, without any presence of antigen or activity systemically. Thus, ATH can be used as a rapid and potent anticoagulant that can inhibit pulmonary fibrin deposition over long periods, without systemic side effects, after a single administration into lungs of premature infants at risk for acute lung injury. ATH exerts an interesting differential effect on epithelial versus fibroblast growth in vitro, that is opposite to the impact by AT. Extensive investigations of ATH immobilized onto polyurethane catheters and endoluminal grafts have shown that the conjugate has significantly greater inhibitory activity against thrombin in vitro and anticoagulant activity in vivo. ATH bound to alveolar matrices can likewise help control excessive local thrombin generation and fibroblast accumulation relative to other cells.

In particular, ATH can be administered when providing mechanical ventilation. Mechanical ventilation can injure the lungs of premature newborns in particular. Therefore, by administering ATH to the lungs of the newborn before or during mechanical ventilation, complications due to fibrin formation in the lungs can be avoided. A single dose of ATH can be sufficient to provide anticoagulant effects in the lungs for an extended period of time. For example, a single dose can last from 6 hours to 1 week in some cases.

The present invention also extends to a particular composition including ATH together with fibrin. ATH can be incubated with fibrin outside the body so that the fibrin binds to the ATH. This composition can then be used to treat blood clots. The composition can be injected or otherwise administered to target a clot. The ATH:Fibrin complex in the composition tends to bind to other fibrin present in the clot. When the ATH:Fibrin complex binds to the surface of the clot, the surface of the clot takes on a net anticoagulant property. This stops the growth of the clot and allows the clot to be broken down.

In one embodiment, a composition for treating blood clots can include antithrombin, heparin, and fibrin. At least 50 wt % of the heparin can be conjugated to antithrombin to form an antithrombin-heparin conjugate. At least a portion of the fibrin can be bound to antithrombin-heparin conjugate. In some cases, at least 50 wt % of the fibrin can be bound to antithrombin-heparin conjugate. The percentage can be higher, such as 90-100 wt % of the fibrin in the composition being bound to the antithrombin-heparin conjugate.

The composition of ATH:Fibrin complex can be prepared by mixing a solution of ATH with a solution of fibrin. The fibrin can be sufficiently dilute or contain a fibrin polymerization inhibitor such as glycine-proline-arginine-proline amide so that the fibrin does not polymerize in the solution. After the fibrin binds to the ATH, if necessary, the ATH:Fibrin can be separated from any unbound fibrin so that the composition does not introduce additional active fibrin into the patient's body.

EXAMPLES

The following examples illustrate embodiments of the disclosure that are presently best known. However, it is to be understood that the following are only exemplary or illustrative of the application of the principles of the present technology. Numerous modifications and alternative compositions, methods, and systems may be devised by those skilled in the art without departing from the spirit and scope of the present disclosure. The appended claims are intended to cover such modifications and arrangements. Thus, while the present disclosure has been described above with particularity, the following examples provide further detail in connection with what are presently deemed to be practical embodiments of the disclosure.

Example 1

Direct incubation of ATH with a polyurethane catheter was carried out as follows. A solution of ATH, spiked with radiolabelled ATH ($^{125}$I-ATH, ATH radiolabeled using Na$^{125}$I (from Perkin Elmer, Woodbridge, ON) and iodo-beads (from Thermo Fisher, Ottawa, ON) according to the manufacturer's instructions), was prepared and then used for incubations with non-activated catheters. Two catheters (15 cm long 7 French Polyurethane catheters from Solomon) were immersed in a cylinder containing 53 mL of 1 mg/mL ATH/$^{125}$I-ATH solution in 1/10 diluted PBS. Fluid was withdrawn up inside each catheter by an attached syringe and held in place by the fixed syringe. The catheters were then incubated for 24 hours at room temperature with stirring via a stirring bar. After the 24 hour incubation, the catheters were removed from the incubation solution and transferred to another vessel for washing. Catheters were washed sequentially in 60 mL volumes of: a) 0.15 M sodium phosphate pH 8.0, b) 2 M NaCl 0.15 M sodium phosphate pH 8.0, c) 0.1% SDS 0.15 M sodium phosphate pH 8.0 (done 3 times in this solution), d) 0.15 M NaCl 0.02 M sodium phosphate pH 7.4 and e) H$_2$O. During each wash, the washing solution was stirred with a stirring bar and washing solution was drawn up and down inside the catheter 50 times with a syringe. After washing, 0.5 cm sample segments (3 per catheter) were cut and taken for gamma-radioactivity counting to determine the amount of radio-labelled ATH remaining bound to the catheter. Each segment was approximately 1 cm$^2$ in total surface area (inside+outside). The results are shown in Table 1:

TABLE 1

| Catheter Sample Number | Counts per Minute | Calculated pmoles ATH |
|---|---|---|
| 1 | 17583 | 0.265 |
| 2 | 13642 | 0.206 |
| 3 | 18070 | 0.273 |
| 4 | 15746 | 0.237 |
| 5 | 14727 | 0.222 |
| 6 | 14567 | 0.220 |
| Average | 15723 | 0.237 |

The values for "Calculated pmoles ATH" were calculated according to the conversion factor that 66,300 counts per minute were equivalent to 1 pmole of ATH. ELISA assays of 0.5 cm segments from sister catheters for the amount of surface ATH (in terms of AT detected by the assay) verified that the total ATH mass on the catheter was also on the order of a tenth of a pmole.

This experiment shows that, surprisingly, free ATH in solution can strongly bind to the surface of the unmodified catheter. This also shows that an ATH flush and lock solution can assist with anticoagulating the catheter at the catheter surface because the ATH will bind to the surface. This is unlike heparin, which does not bind to the surface of catheters. The ATH remained bound after copious washing with buffer, detergent and high salt. In contrast, heparin has not been found to bind to polyurethane surfaces.

Example 2

Direct incubation of ATH with a polyurethane catheter with drying can be carried out as follows. The following example illustrates in detail how unmodified covalent antithrombin-heparin (ATH) can be coated onto non-reactive, passive, polymer surfaces without prior modification or activation of either ATH or the polymer surface. A solution of ATH in an appropriate buffer (with pH ranging from 4.0 to 10.0, and in some cases at about 7.4) is prepared with ATH concentration (in terms of the AT moiety) ranging from 0.01 mg/mL to 10 mg/mL and in some cases at about 1 mg/mL. Up to 20 catheters (such as 15 cm long Polyurethane catheters) are immersed in a cylinder containing 53 mL of the ATH solution. Fluid is withdrawn up inside each catheter by an attached syringe and held in place by the fixed syringe. The catheters are then incubated for 24 hours at room temperature with stirring via a stirring bar. After the 24 hour incubation, the syringes are detached, the catheters are removed from the incubation solution, each catheter is held vertically with the bottom end touching a cellulose filter paper, and fluid is allowed to drain by gravity from inside and outside of the catheter for a period of time (typically around 1 minute). The catheters are then allowed to hang vertically for drying (evaporation of solvent) with bottom tip not touching any solid surface. Drying for up to 48 hours (in some cases about 18 hours) can be in either: still air at room temperature, still nitrogen gas at room temperature, still noble gas at room temperature, an open atmosphere of gas heated up to 60 degrees Celsius or a vacuum (for lyophilization). Once dried, the catheters are used in vitro or put in sealed bags (with membranes that are gas permeable) and sterilized by exposure to ethylene oxide for future use in patients or other medical applications.

Example 3

Effectiveness of ATH Inhibition of Coagulation Factors on Endothelial Cells That Line Blood Vessels (Artificial Blood Vessel Surface). In vitro investigations of coagulation factor inhibition by ATH have primarily been carried out in plasma or buffer solutions containing purified proteins. In vivo, the endothelial surface can modulate coagulation in various ways, such as providing protein receptor binding sites for thrombin which alter its activity (e.g. thrombomodulin (TM)), and expressing anticoagulant glycosaminoglycan (GAG) molecules (e.g. heparan sulfate (HS)). The objective of this study was to compare ATH and AT+H anticoagulant activities in the presence of endothelium.

Human umbilical vein endothelial cells (HUVEC), EBM-2 media and EGM-2MV Bullet Kits were purchased from Lonza (Walkersville, Md., USA). Minimal Essential Media (MEM) was purchased from Invitrogen. IIa and Xa were from Enzyme Research Laboratories (South Bend, Ind., USA). Human normal pooled plasma and purified human AT were from Affinity Biologicals (Ancaster, ON, CA). Heparin, hexadimethrine bromide (polybrene), heparan sulfate and gelatin were purchased from Sigma (Mississauga, ON, CA). Fibrinogen (plasminogen, fibronectin, FXIII-depleted) and recombinant human thrombomodulin were from American Diagnostica Inc. (Stamford, Conn., USA). S-2238 and S-2222 were from Diapharma (West Chester, Ohio, USA). ATH was produced as previously described. All other reagents were of reagent grade quality.

HUVEC were cultured under sterile conditions on tissue culture treated plasticware (Primaria, BD, Mississauga, ON, CA) coated with 2% gelatin. For experiments, cells were seeded in 96-well plates at 20000-40000 cells/mL and grown to confluence in EBM-2 media supplemented with EGM-2MV Bullet kit, in a humidified air—5% $CO_2$ atmosphere. Cells were used between passages 2 and 5.

Second order rate constant ($k_2$) values for ATH and non-covalent AT+H inhibition of IIa and Xa were measured at 37° C. by a discontinuous assay under pseudo-first order conditions (inhibitor:enzyme ratio=10:1). IIa, Xa, AT, UFH and ATH were diluted in Minimal Essential Media (MEM) containing 10 mM HEPES pH 7.4 and 0.1% (w/v) PEG3000 (MEMPH). IIa or Xa were incubated with AT+H or ATH in wells of a 96-well plate containing confluent HUVEC monolayers. Monolayers were washed with MEMPH before addition of reaction components. The molar ratios of H:AT in the non-covalent AT+H mixtures were 23:1 and 10:1 for reactions with IIa and Xa respectively. These H:AT ratios were previously found to produce maximal $k_2$ values for inhibition in the absence of HUVEC. After incubating for various time intervals, reactions were stopped by addition of 1.25 mg/mL polybrene in TSP buffer (20 mM Tris-Cl, 150 mM NaCl, 0.6% (w/v) PEG8000 pH 7.4) containing 0.4 mg/mL of the appropriate chromogenic substrate (S-2238 for IIa or S-2222 for Xa). Residual enzyme activities in each well were measured as the change in $A_{405}$ over time using a SpectraMax Plus 384 spectrophotometer (Molecular Devices, Sunnyvale, Calif., USA). The $k_2$ values were calculated by taking the negative value of the slope from plots of residual enzyme activity versus time of inhibition prior to polybrene/substrate addition and dividing this negative value for slope by the inhibitor (i.e. ATH or AT) concentration. Identical assays were also performed on a plastic surface (no HUVEC) for comparison, using untreated Falcon Pro-Bind Flat Bottom 96-well plates (BD, Franklin Lakes, N.J., USA).

In separate experiments, wells containing HUVEC monolayers were washed with MEMPH, and 20 µL of 2 nM IIa (diluted in MEMPH) was added to multiple wells. Following a 3 min incubation at 37° C., 80 µL of MEMPH containing 1 mg/mL human fibrinogen and varying concentrations of AT+H or ATH (0-1.25 nM ATH or AT with H:AT ratio of 23:1) was added simultaneously to all wells. Fibrin clot formation at 37° C. was monitored turbidimetrically, by measuring $OD_{350}$ using a SpectraMax Plus 384 spectrophotometer. The lag time to clot formation was defined as the time for the $OD_{350}$ to reach 0.005. If the $OD_{350}$ did not reach 0.005 after 90 min, the lag time was assigned as 90 min. Assays were also performed on plastic (no HUVEC) for comparison. In some assays performed on plastic, 2 nM IIa was mixed with 10 nM thrombomodulin (TM) or 5 M heparan sulfate (HS) prior to the 3 min incubation step.

Results are expressed as mean±SEM. Analysis of statistical significance was performed using Student's t-test, where p<0.05 was considered significant. Student's t-test was performed using Minitab 13 for Windows.

Figure 1B:
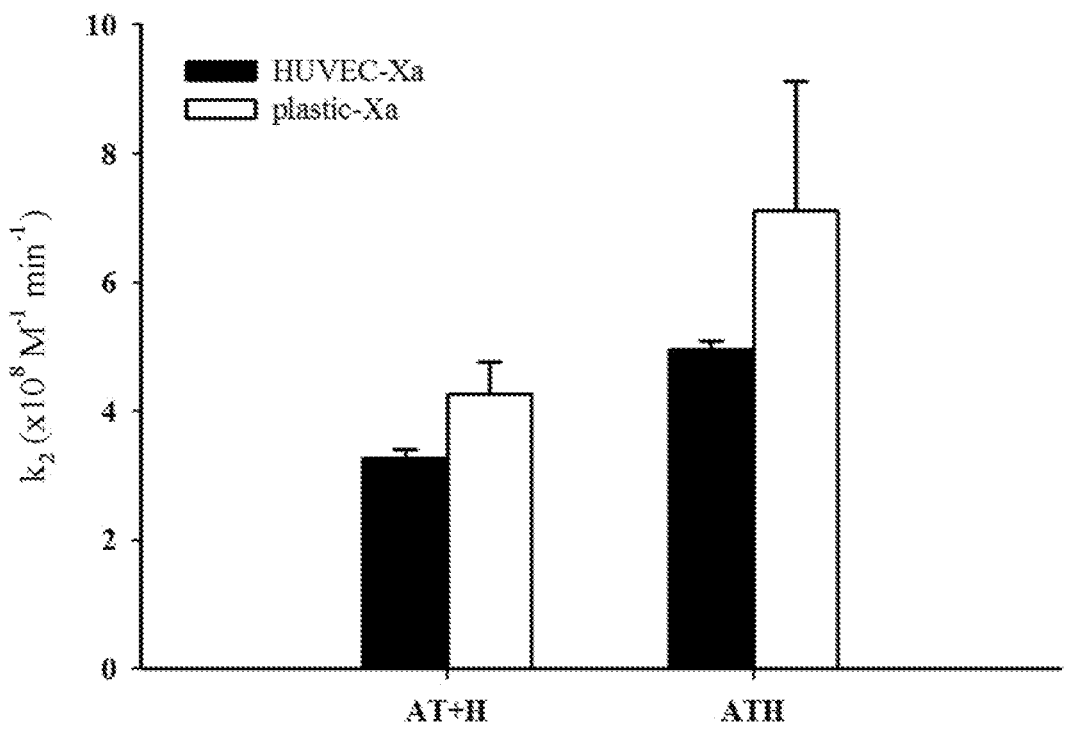
FIG. 1B is a graph of second order rate constant ($k_2$) values for ATH and non-covalent AT+H inhibition of Xa in accordance with examples of the present disclosure.

To assess the effect of endothelium on heparin-catalyzed inhibition of IIa and Xa by non-covalent AT+H or ATH, $k_2$ values were determined for the rates of inhibition of these proteases in the absence or presence of a HUVEC monolayer. FIGS. 1A and 1B show rate of inhibition of coagulation factors by AT+H and ATH in the presence of endothelium. $K_2$ values were determined for inhibition of IIa (A) and Xa (B) by ATH and AT+H in either plastic surface wells, or wells covered with a HUVEC monolayer. $K_2$ values were measured under pseudo first order conditions using a discontinuous method. The molar ratios of H:AT in the AT+H mixture were 23:1 (A) and 10:1 (B), which has been previously shown to give maximal $k_2$ values for inhibition of IIa and Xa respectively. Data represents mean±SEM (n≥5). In the absence of HUVEC, the $k_2$ values for inhibition of IIa and Xa by ATH were higher than the $k_2$ values for inhibition by non-covalent AT+H (FIGS. 1A and 1B). The degree of increase was greatest for IIa, at 2.3-fold. When endothelium was present, ATH inhibition of IIa and Xa was, again, more rapid than with AT+H (FIGS. 1A and 1B). In comparison to plastic, the absolute $k_2$ values for both ATH and AT+H on endothelial cells were significantly decreased (p<0.05) in the case of IIa (FIG. 1A), and slightly but non-significantly decreased for Xa (p>0.1) (FIG. 1B).

Figure 2:
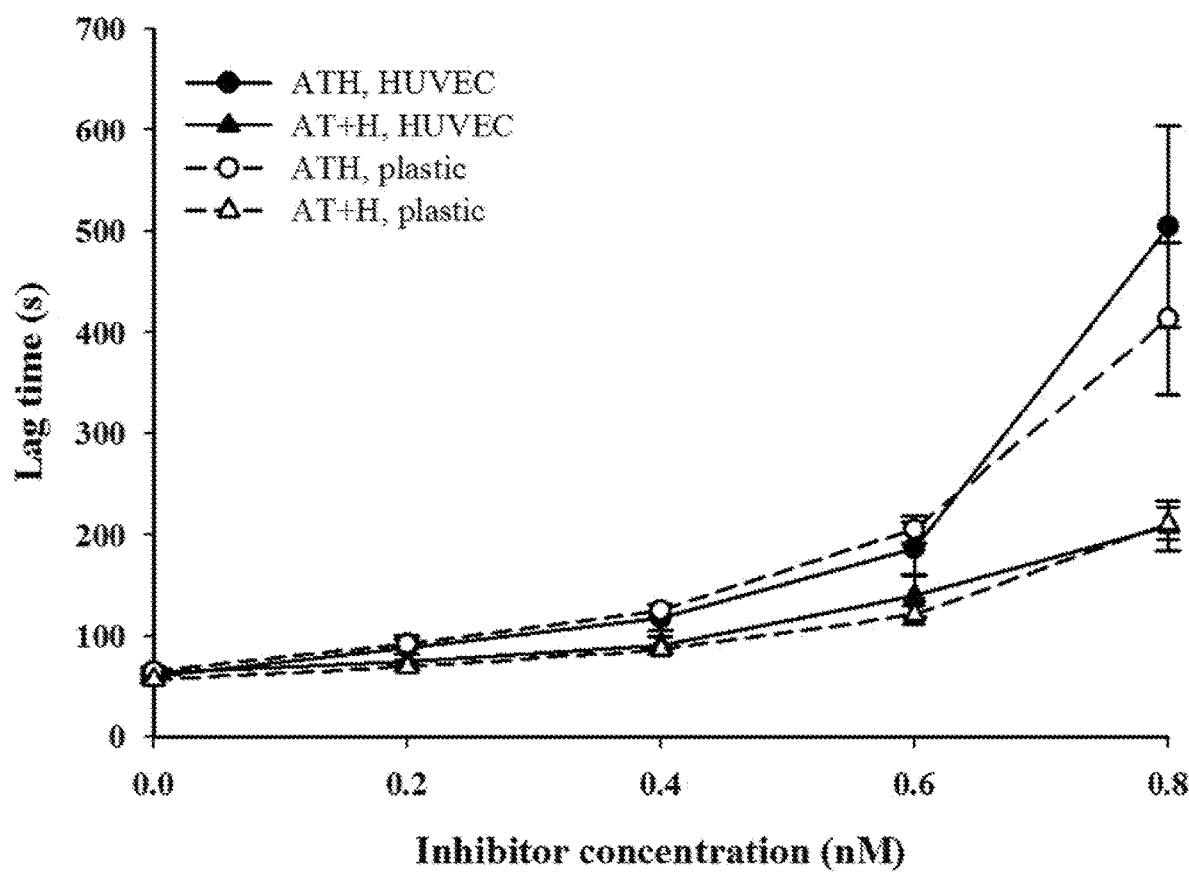
FIG. 2 is a graph of lag time of inhibition of IIa-induced fibrin formation by ATH and AT+H in the presence of endothelium in accordance with examples of the present disclosure.

Inhibition of IIa was further investigated by a fibrin formation assay, in which IIa was incubated in wells with or without a HUVEC monolayer present, followed by addition of fibrinogen and anticoagulants to the wells. FIG. 2 shows inhibition of IIa-induced fibrin formation by AT+H and ATH in the presence of endothelium. IIa was incubated in plastic or HUVEC-coated wells, before addition of a mixture of purified fibrinogen, $CaCl_2$ and AT+H or ATH. The final concentration of IIa was 0.4 nM. Final inhibitor (AT or ATH) concentrations are indicated on the X-axis, and the molar ratio of H:AT in the AT+H mixture was 23:1. Fibrin formation was monitored turbidimetrically, and the lag time represents the time to reach $OD_{350}$=0.005. Data represent mean±SEM (n≥5). FIG. 2 illustrates that, in contrast to the rate experiments, the presence of endothelium did not have an effect on inhibition of IIa fibrinogen-cleaving activity by either ATH or AT+H. As with the rate experiments, ATH was more effective than AT+H at preventing fibrin formation by IIa.

Figure 3A:
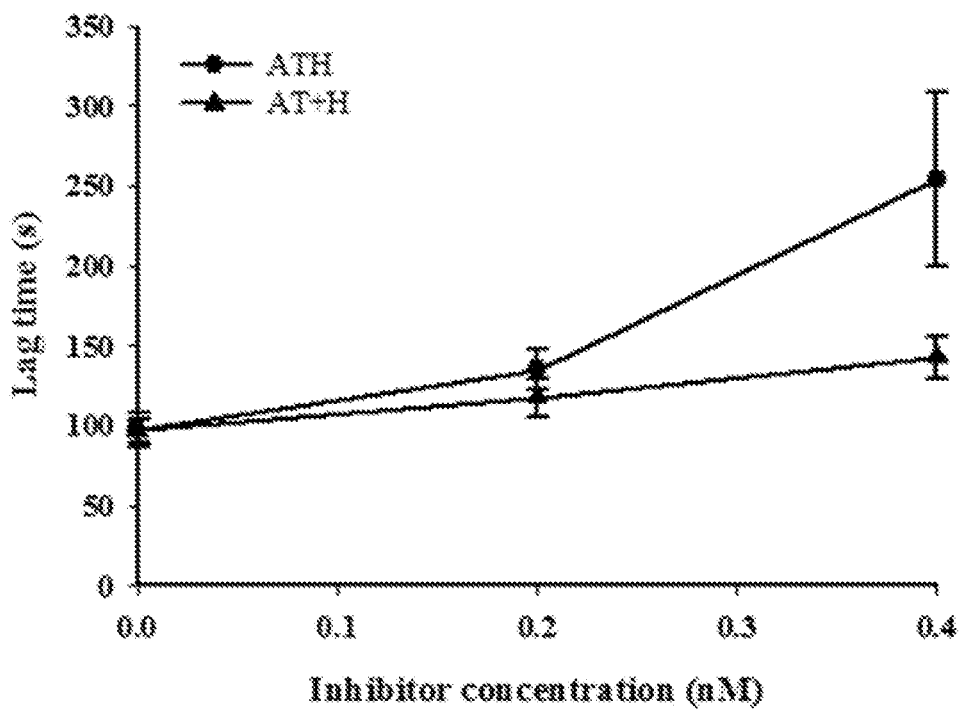
FIG. 3A is a graph of lag time of inhibition of fibrin formation induced by IIa bound to heparan sulfate (HS) in accordance with examples of the present disclosure.
Figure 3B:
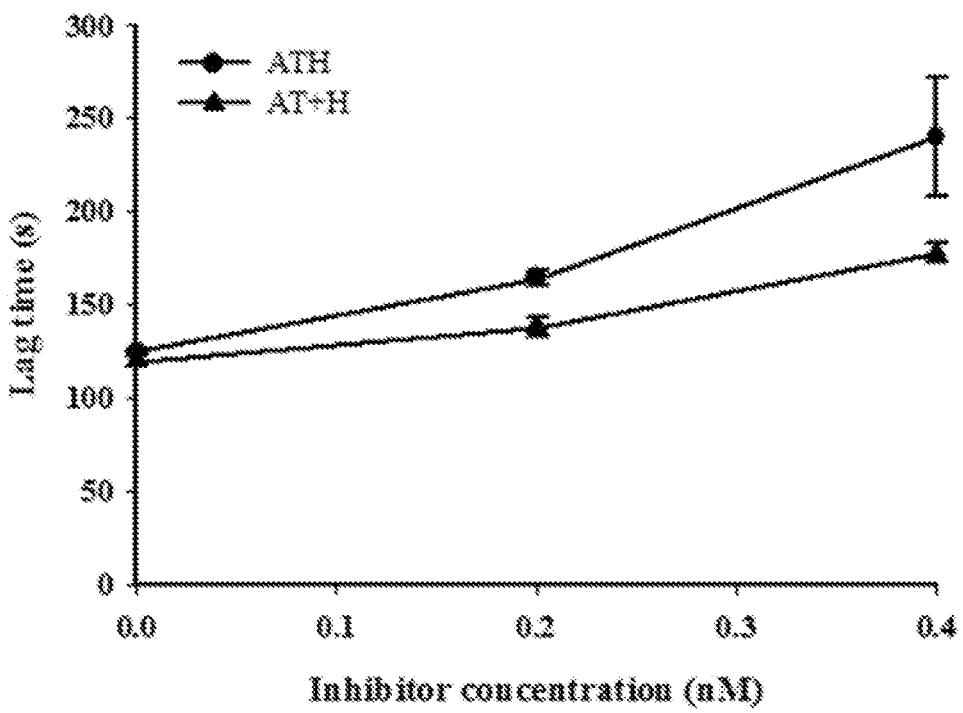
FIG. 3B is a graph of lag time of inhibition of fibrin formation induced by IIa bound to thrombomodulin (TM) in accordance with examples of the present disclosure.

The two molecules which constitute the major IIa binding sites on the endothelial surface are HS and TM. To determine if IIa binding to either of these molecules affected anticoagulant activity, soluble HS or TM were pre-incubated with IIa and fibrin formation assessed in the absence or presence of ATH or AT+H. HS did not affect IIa-induced fibrin formation (onset time=97.3±6.6 s vs. 95.4±6.4 s in the presence and absence of HS respectively, n=9). The presence of TM significantly delayed fibrin formation, with an onset time of 122.4±1.7 s, compared to 97.9±6.4 s in the absence of TM (p=0.003, n≥8). FIGS. 3A and 3B show inhibition of fibrin formation induced by IIa bound to HS or TM. IIa was mixed with excess HS (A) or TM (B) before fibrin formation assays were conducted in plastic wells, as described for FIG. 2. Final concentrations of IIa, HS and TM were 0.4 nM, 1 μM and 4 nM respectively. Final inhibitor (AT or ATH) concentrations are indicated on the X-axis, and the molar ratio of H:AT in the AT+H mixture was 23:1. Data represent mean±SEM (n≥4). ATH maintained its superior anticoagulant function compared to AT+H in the presence of both HS (FIG. 3A) and TM (FIG. 3B).

Example 4

Flush Lock Of Catheters Using ATH Solution. A solution of ATH is prepared in 0.15 M NaCl, with or without a buffer (such as 0.05 M HEPES) set at pH 7.4. The ATH concentration in this solution is about 1.5 U/mL in terms of anti-factor Xa activity but can in some cases range from 0.01 U/mL to 100 U/mL anti-factor Xa activity. The ATH solution is sterilized by filtration through a sterile filter possessing 0.2 micrometer pores within a laminar flow hood with sterile air flow. While still within the sterile environment, the sterile filtered ATH solution is either sealed within sterile bottles containing a septum for later withdrawal into sterile syringes just before use or measured amounts are taken up into sterile syringes that are capped.

After a catheter is inserted into a vein or artery of a subject or patient, a syringe containing about 2 mL (in some cases from 0.1 mL to 50 mL total volume) of the sterilized ATH solution prepared as described above is connected to the exterior end of the catheter and all of the ATH solution in the syringe is injected into the catheter, followed by sealing of the catheter with a sterile cap.

After periods ranging from 1 hour to 7 days, the cap can be removed and replaced by a syringe so that a blood sample can be withdrawn or medication can be injected. After withdrawal of blood or injection of medication, the blood sampling or medication delivering syringe is replaced with another syringe containing ATH solution similar to the previous one and the ATH solution injected, followed by capping of the catheter as before. This process is repeated as long as necessary until the catheter is removed.

Example 5

Treatment of Ligneous Conjunctivitis. A solution of ATH is prepared in 0.15 M NaCl, with or without a buffer (such as 0.05 M HEPES) set at pH 7.4. The ATH concentration in this solution would typically be around 1 milligram/mL (in terms of the AT content) but could range from 0.001 milligrams/mL to 11 milligrams/mL. The ATH solution is sterilized by filtration through a sterile filter possessing 0.2 micrometer pores within a laminar flow hood with sterile air flow.

A patient requiring treatment to prevent formation of ligneous conjunctivitis on tissue surfaces outside of the vascular system receives aliquots of the ATH containing solution on a regular basis. In the case of ligneous conjunctivitis of the eye, 1 or more drops (approximate drop volume of around 10 microliters to 100 microliters) of the ATH solution described above are applied one or more times per day, depending on the severity of the particular patient's disease. This process is repeated on an ongoing basis for lifelong treatment of the patient.

Example 6

Recent preliminary data suggest that ATH exerts an interesting differential effect on epithelial versus fibroblast growth in vitro that is opposite to impact by AT (see Table 2 below). Extensive investigations of ATH immobilized onto polyurethane catheters and endoluminal grafts have shown that the ATH conjugate had significantly greater inhibitory activity against thrombin in vitro and anticoagulant activity in vivo. These results suggest that ATH bound to alveolar matrices can help control excessive local thrombin generation and fibroblast accumulation relative to other cells.

TABLE 2

Effect of AT and ATH on growth of lung cells in MEM medium

| | Percent Change in Cell Number Relative to Control | |
|---|---|---|
| Treatment | Epithelial Lung Cells | Fibroblast Lung Cells |
| 500 nM AT | −19.3 ± 3.3 | −0.141 ± 1.76 |
| 500 nM ATH | 29.1 ± 13.6** | 13.9 ± 4.16*** |

Primary newborn rat lung cell cultures were grown in 24 well plate wells over 1 day in a moist 5% $CO_2$/95% air atmosphere at 37° C. in MEM medium supplemented with either antithrombin (AT) or covalent AT-heparin (ATH). Cells were then released from the monolayer using trypsin and total cell number determined using a hemocytometer. Results are expressed as the mean±SEM (n=5) of percent change in cell number relative to control cultures in unsupplemented MEM medium. Significant differences of results with ATH from those with AT in the same group of cells are indicated (*,  and * mean P=0.002, P=0.026 and P=0.027, respectively). While AT alone significantly inhibited proliferation of epithelial but not fibroblast cells, ATH preferentially enhanced epithelial growth relative to fibroblasts.

Example 7

Figure 4A:
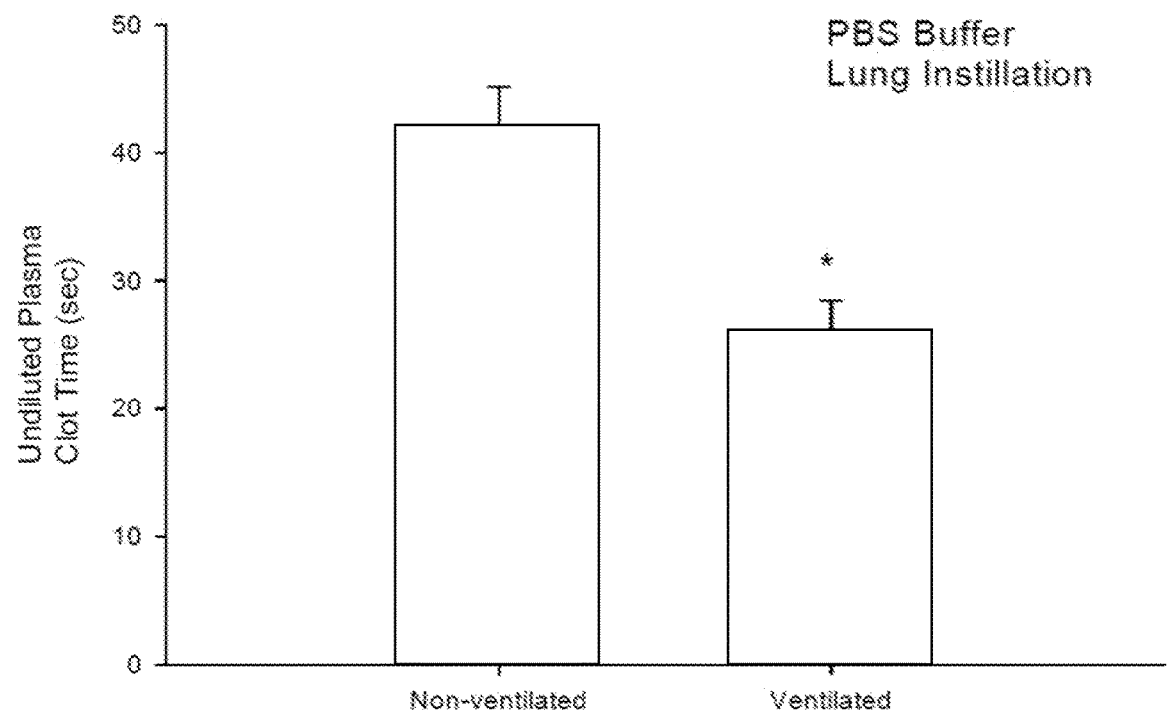
FIG. 4A is a graph of clot time of plasma samples from rats treated with intra-pulmonary PBS buffer, with and without high volume mechanical ventilation for one hour, in accordance with examples of the present disclosure.
Figure 4B:
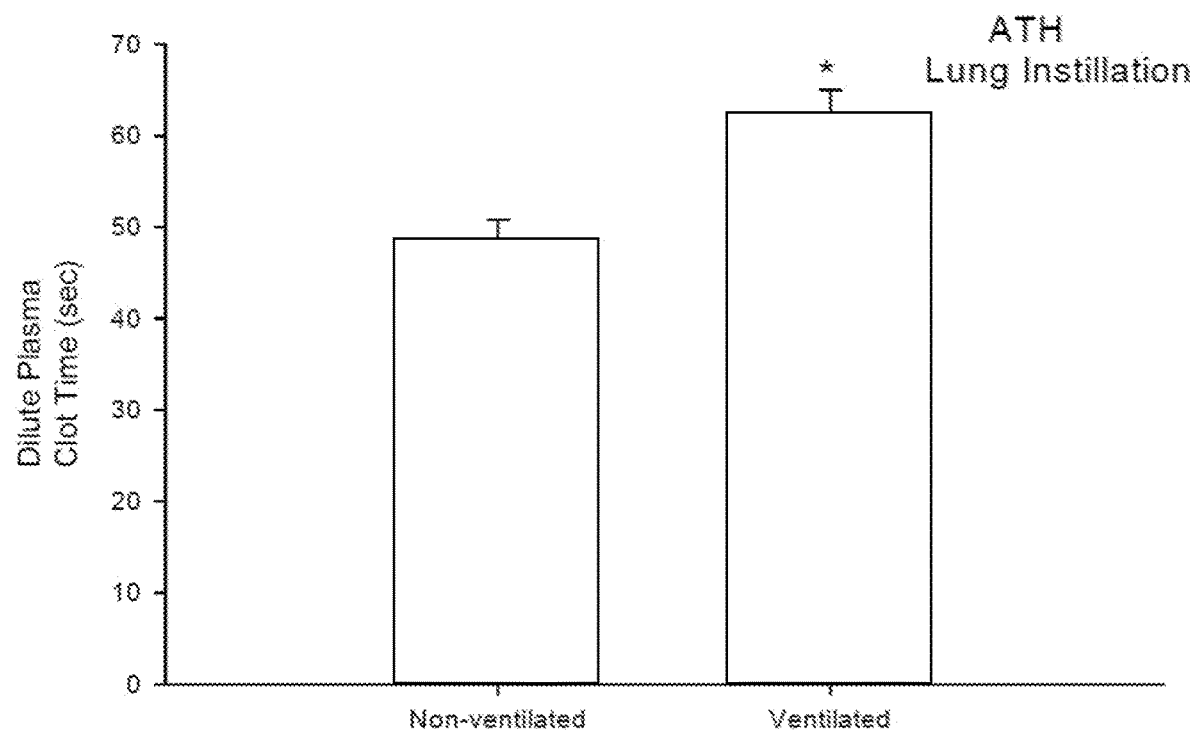
FIG. 4B is a graph of clot time of plasma samples from rats treated with intra-pulmonary ATH, with and without high volume mechanical ventilation for one hour, in accordance with examples of the present disclosure.

Investigation of ATH treatment of lungs under condition of acute stress/injury. Preliminary experiments have been conducted using intra-tracheal ATH in newborn animals that were randomized to either normal respiration or 1 h high volume mechanical ventilation. FIG. 4 shows clot times of recalcified plasma samples from citrated blood taken from 2-6 day old rats treated with either intra-pulmonary ATH or PBS buffer, with or without high volume mechanical ventilation for 1 hour. Coagulation assays strongly showed that, relative to controls instilled with buffer, ATH eliminated the reduced plasma clot time from ventilation-associated systemic tissue factor (TF) activity (see FIG. 4). Since TF-related pulmonary thrombin generation and fibrin formation is apparent, direct neutralization of the key VIIa-TF complex by ATH conjugate could block activation of coagulation in the lung where plasma inhibitors will be sparse.

Example 8

Figure 5:
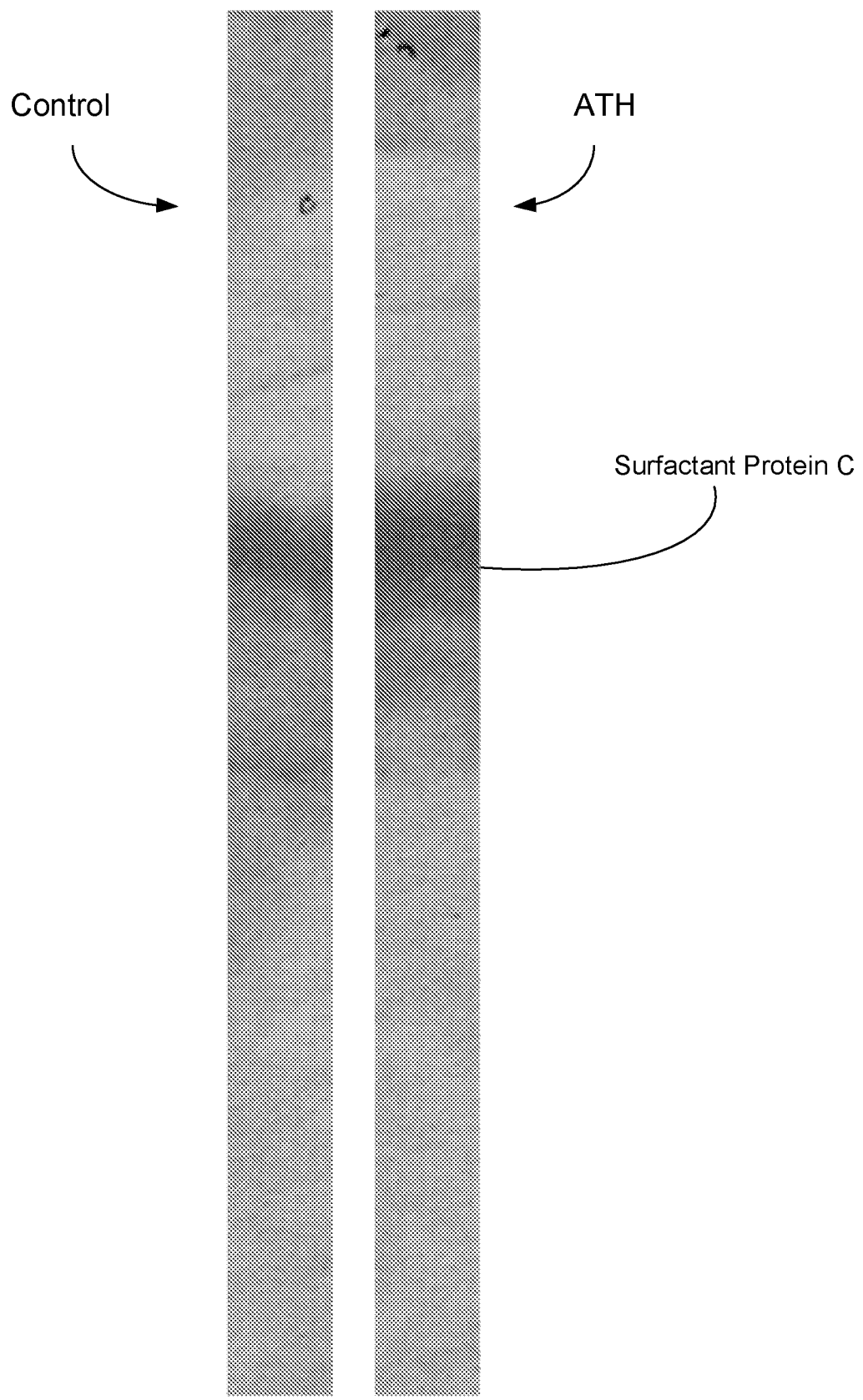
FIG. 5 shows Western immunoblots of cell media incubated with either buffer (control) or ATH in accordance with examples of the present disclosure.

Experiments were conducted to determine the effect of ATH on lung cell surfactant production to measure the potential for ATH instillation in the lung (to prevent RDS or lung damage from mechanical ventilation) to increase surfactant levels for preventing airspace collapse and improving gas transfer. The following preliminary data were collected (see FIG. 5). Fetal distal lung epithelium (FDLE) was isolated from 20 day old fetal rats and cultured in 24 well culture plate wells. Culture medium was either supplemented with 100 µg/mL ATH or control buffer. FIG. 5 shows Western immunoblots of cell media produced by rat fetal distal lung epithelium (FDLE) cells incubated with either buffer or ATH (100 µg/mL culture media), that were probed for surfactant protein C. The western immunoblots of cell media showed an increase in surfactant protein C produced by FDLE cells incubated with ATH (100 µg/mL culture media).

Example 9

ATH:Fibrin Anticoagulant for Treatment of a Clot. The following is a proposed methodology for preparation of ATH bound to Fibrin monomer that can be injected to target a clot in a patient and make the clot surface have a net anticoagulant property. Use of ATH:Fibrin may make for a very effective clot neutralizing agent that can be used at a low concentration relative to injection of ATH alone since the ATH:Fibrin complex will tend to bind to other fibrin if present in significant concentration, such as that on a clot containing polymerized fibrin. Unlike ATH already bound to fibrin, free ATH would end up on other targets besides the fibrin clot and, therefore, may need to be administered at much higher concentrations. Below, is a method to prepare ATH bound to Fibrin monomer and administer it to a patient containing a clot.

A stock solution of Fibrin monomer in acetic acid is prepared as follows. Commercially available fibrinogen (Enzyme Research Laboratories, South Bend, Ind., USA) is used. In previous experiments, the following protocol was used to prepare stocks of soluble fibrin in solutions. Initially, any contaminating fibronectin was removed from the commercial fibrinogen by 2 incubations of 15 mL of 130 µM fibrinogen (molecular mass 340000 Da) with 5 mL of gelatin agarose (Sigma, Mississauga, Ontario, Canada) for 30 min, followed by centrifugation and collection of the fibrinogen containing supernatant. Fibrinogen concentration was determined by absorbance at 280 nm using absorbance of 10 mg/mL=15.1 (after correction for light scatter at 320 nm using the equation corrected $A_{280}=A_{280}-1.7\times A_{320}$). Soluble fibrin monomer was prepared by the following method. Purified fibrinogen (60-100 µM) was incubated with 2 nM thrombin (Enzyme Research Laboratories, South Bend, Ind., USA) at 37° C. for 4-6 hours, followed by centrifugation at 2000 g for 5 min. The fibrin polymer pellet was placed in a dialysis bag (12000-14000 molecular weight cut-off), dialyzed versus $H_2O$ (4° C.) to remove fibrinopeptides A and B and then further dialyzed versus 0.02 M acetic acid until the fibrin dissolved (~8 hours). Concentration of the soluble fibrin in solution was obtained by absorbance at 280 nm and using a molecular weight of 340000 and absorbance of 10 mg/mL=14.0. Typically, 100 µM of soluble fibrin was obtained and stored at –80° C.

To prepare solutions of fibrin for binding to ATH, 6 volumes of the soluble fibrin in 0.02 M acetic acid is neutralized with 4 volumes of 1 M Tris-HCl pH 7.5 containing 10 mM GPRP-NH$_2$ (Sigma, Mississauga, Ontario, Canada) to block polymerization of the fibrin under neutral conditions. The resultant neutralized 40000 nM soluble fibrin monomer could be diluted further or kept at that concentration prior to combining with ATH. Although solutions with a range of molar ratios of fibrin:ATH can be prepared, ATH can be added to the fibrin (at pH around 7.5 in the presence of GPRP-NH$_2$) at approximately equal molar concentrations up to a slight molar excess (around 10%) relative to the fibrin. In a typical experiment, 1 volume of 40000 nM ATH in 0.02 M Tris-HCl 0.15 M NaCl 0.6% polyethylene glycol 8000 pH 7.4 (TSP) containing 0.01 M GPRP-NH$_2$ is mixed rapidly with an equal volume of the neutralized 40000 nM neutralized fibrin solution. The resultant mixture, designated as ATH:Fibrin solution 1, contains 20000 nM ATH+20000 nM soluble fibrin monomer.

ATH+Fibrin solutions can be injected intravenously into patients who have a clot in order to neutralize the procoagulant activity of the clot, so that the body's own native fibrinolytic system can successfully digest the clot to remove it. The dose of ATH:Fibrin product to be delivered to the patient can vary widely dependent on the degree of thrombosis or coagulation activity or clot size in the patient. Using the ATH:Fibrin solution described above, anywhere from 0.01 mL/kg body weight to 10 mL/kg body weight can be administered by intravenous injection, with 0.5 mL/kg body weight being most common. Other options to prepare ATH+Fibrin monomer solutions include rapidly diluting the 100 µM fibrin in 0.02 M acetic acid with 0.02 M Tris-HCl 0.15 M NaCl 0.6% polyethylene glycol 8000 pH 7.4 (TSP) to a concentration of <100 nM where the fibrin will not polymerize very quickly. An equal volume of ATH at the same concentration is then rapidly mixed into the dilute fibrin solution and the resultant mixture injected at doses ranging from 0.1 mL/kg body weight to 10 mL/kg body weight, with 2 mL/kg body weight being common.

It is to be understood that the above-referenced arrangements are illustrative of the application for the principles of the present disclosure. Thus, while the present technology has been described above in connection with the exemplary embodiments, it will be apparent to those of ordinary skill in the art that numerous modifications and alternative arrangements can be made without departing from the principles and concepts of the disclosure as set forth in the claims.

What is claimed is:

1. A medical device having reduced thrombogenicity, the medical device comprising a polymeric surface having a compound bonded to the polymeric surface of the medical device, wherein the compound includes an antithrombin-heparin conjugate,
wherein at least 98% of heparin chains in the antithrombin-heparin conjugate have a molecular weight greater than 5,000 Daltons,
wherein the antithrombin-heperain conjugate is conjugated at the aldose terminus aldehyde on the heparin and a lysyl or N-terminal amino group on antithrombin.

2. The medical device of claim 1, wherein the medical device is selected from the group consisting of an intravenous catheter, an intra-arterial catheter, a peripherally inserted central catheter, a central catheter, a Swan-Ganz catheter, a coronary stent, an arteriovenous shunt, a mechanical valve, an artificial organ, a dialysis catheter, a dialysis blood circuit line, a dialysis membrane, an extracorporeal membrane oxygenation line, an extracorporeal membrane oxygenation membrane, an in vivo prosthetic, and a blood storage container.

3. A flush and lock system, comprising:
an intravenous or intra-arterial catheter;
a flush and lock solution to flush and lock the catheter, wherein the flush and lock solution comprises from 0.01 mg/mL to 10 mg/mL of an antithrombin-heparin conjugate, wherein at least 98% of heparin chains in the antithrombin-heparin conjugate have a molecular weight greater than 5,000 Daltons, and wherein the antithrombin-heperain conjugate is conjugated at the aldose terminus aldehyde on the heparin and a lysyl or N-terminal amino group oil antithrombin.

4. A method of maintaining patency of a catheter using the flush and lock system of claim 3, comprising:
inserting the catheter into a vein or artery of a subject so that an interior opening of the catheter opens inside the vein or artery and an exterior opening of the catheter opens outside the subject;
injecting the solution into the catheter through the exterior opening of the catheter; and
sealing the exterior opening of the catheter such that at least a portion of the solution comprising the antithrombin-heparin conjugate remains within the catheter.

5. The flush and lock system of claim 3, further comprising a syringe configured to inject the flush and lock solution into the catheter.

6. The medical device of claim 1, wherein the polymeric surface is selected from the group consisting of a polyurethane surface, a polyethylene surface, a polypropylene surface, a polytetrafluoroethylene surface, a polydimethylsiloxane surface, and ethylene-acrylic acid copolymer surface, a Dacron surface, a polyester-polyurethane surface, a polyurethane-polycarbonate surface, a polyvinyl chloride surface, a silicone surface, a latex rubber surface, a nitinol surface, a Nylon surface, a polyethylene terephthalate surface, a polystyrene surface, or combinations thereof.

7. A medical device having reduced thrombogenicity, the medical device comprising a polyurethane surface with a compound bonded to the polyurethane surface, wherein the compound includes an antithrombin-heparin conjugate with at least 98% of heparin chains in the antithrombin-heparin conjugate having a molecular weight greater than 5,000 Daltons, and wherein the antithrombin-heperain conjugate is conjugated at the aldose terminus aldehyde on the heparin and a lysyl or N-terminal amino group on antithrombin.

8. The medical device of claim 7, wherein the medical device is selected from the group consisting of an intravenous catheter, an intra-arterial catheter, a peripherally inserted central catheter, a central catheter, a Swan-Ganz catheter, a coronary stent, an arteriovenous shunt, a mechanical valve, an artificial organ, a dialysis catheter, a dialysis blood circuit line, a dialysis membrane, an extracorporeal membrane oxygenation line, an extracorporeal membrane oxygenation membrane, an in vivo prosthetic, and a blood storage container.

9. The medical device of claim 7, wherein at least 98% of the heparin chains in the antithrombin-heparin conjugate have at least 18 monosaccharide units.

10. The medical device of claim 1, wherein the heparin chains in the antithrombin-heparin conjugate have a molecular weight up to 50,000 Daltons.

11. The medical device of claim 1, wherein the heparin chains in the antithrombin-heparin conjugate have a molecular weight up to 30,000 Daltons.

12. The medical device of claim 1, wherein the antithrombin-heparin conjugate is bonded directly to the polymeric surface of the medical device without linking groups between the antithrombin-heparin conjugate and the polymeric surface of the medical device.

13. The medical device of claim 1, wherein the antithrombin-heparin conjugate is a single molecule layer thick on the polymeric surface.

14. The medical device of claim 1, wherein the compound consists essentially of the antithrombin-heparin conjugate.

15. The medical device of claim 7, wherein the heparin chains in the antithrombin-heparin conjugate have a molecular weight up to 50,000 Daltons.

16. The medical device of claim 7, wherein the heparin chains in the antithrombin-heparin conjugate have a molecular weight up to 30,000 Daltons.

17. The medical device of claim 7, wherein the antithrombin-heparin conjugate is bonded directly to the polymeric surface of the medical device without linking groups between the antithrombin-heparin conjugate and the polymeric surface of the medical device.

18. The medical device of claim 7, wherein the antithrombin-heparin conjugate is a single molecule layer thick on the polymeric surface.

19. The medical device of claim 7, wherein the compound consists essentially of the antithrombin-heparin conjugate.

* * * * *